US012799212B2

(12) United States Patent
Felices et al.

(10) Patent No.: US 12,799,212 B2

(45) Date of Patent: Nov. 17, 2026

(54) CLEC12A ANTIBODY FRAGMENT SEQUENCES AND METHODS

(71) Applicant: REGENTS OF THE UNIVERSITY OF MINNESOTA, Minneapolis, MN (US)

(72) Inventors: Martin Felices, Circle Pines, MN (US); Jeffrey S. Miller, North Oaks, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1088 days.

(21) Appl. No.: 17/768,793

(22) PCT Filed: Oct. 14, 2020

(86) PCT No.: PCT/US2020/055468

§ 371 (c)(1),
(2) Date: Apr. 13, 2022

(87) PCT Pub. No.: WO2021/076545

PCT Pub. Date: Apr. 22, 2021

(65) Prior Publication Data

US 2024/0117053 A1 Apr. 11, 2024

Related U.S. Application Data

(60) Provisional application No. 62/916,340, filed on Oct. 17, 2019.

(51) Int. Cl.

| | |
|---|---|
| ***C07K 16/28*** | (2006.01) |
| ***A61K 47/68*** | (2017.01) |
| *A61K 39/00* | (2006.01) |

(52) U.S. Cl.

CPC ...... *C07K 16/2851* (2013.01); *A61K 47/6849* (2017.08); *A61K 39/00* (2013.01); *C07K 2317/24* (2013.01); *C07K 2317/31* (2013.01)

(58) Field of Classification Search

CPC ............ C07K 16/2851; C07K 2317/24; C07K 2317/31; C07K 2317/22; C07K 2317/569;

(Continued)

(56) References Cited

U.S. PATENT DOCUMENTS 9,090,876 B2 7/2015 Velardi et al.
9,155,798 B2 10/2015 Vallera (Continued)

FOREIGN PATENT DOCUMENTS

CN 103467599 A 12/2013
EP 2332994 6/2011

(Continued)

OTHER PUBLICATIONS

Raaphorst et al. Eur J Immunol. Jan. 1992;22(1):247-51. PMID: 1730252. (Year: 1992).*

(Continued)

*Primary Examiner* — Misook Yu

(74) *Attorney, Agent, or Firm* — Mueting Raasch Group

(57) ABSTRACT

An anti-CLEC12A polypeptide generally includes an amino acid sequence having at least 90% amino acid similarity to SEQ ID NO:14. In some embodiments, anti-CLEC12A polypeptide may be incorporated into an anti-CLEC12A biologic. In some of these embodiments, the anti-CLEC12A biologic can be a bi-specific Killer engager molecule (BiKE), a tri-specific Killer engager molecule (TriKE), a tetra-specific Killer engager molecule (TetraKE), a penta-specific Killer engager molecule (PentaKE), a bi-specific T cell engager molecule (BiTE), a tri-specific T cell engager molecule (TriTE), tetra-specific T cell engager molecule (Continued)

```
Clone 1    (1)  QVQLQESGGGLVQPGGSLRLSCAASGDRFSNDVMAWVRQAPGKGLEWVSAIVTQDGSTYYADSVKGRFTI
Clone 3    (1)  QVQLLESGGGLVQPGGSLRLSCAASGVRVSAQFMSWVRQAPGKGLEWVSSIYKKNGSTYYADSVKGRFTI
Clone 9    (1)  QVQLLESGGGLVQPGGSLRLSCAASGYSITDQDMSWVRQAPGKGLEWVSGILATSGSTYYADSVKGRFTI
Clone 10   (1)  QVQLLESGGGLVQPGGSLRLSCAASGVNVTADDMSWVRQAPGKGLEWVSTIDGGDGSTYYADSVKGRFTI
Clone 11   (1)  QVQLLESGGGLVQPGGSLRLSCAASGYRLSNDIMAWVRQAPGKGLEWVSAIVDTDGSTYYADSVKGRFTI
Clone 17   (1)  QVQLLESGGGLVQPGGSLRLSCAASGFRFTAQDMSWVRQATGKGLEWVSTIATNDGSTYYADSVKGRFTI
Clone 23   (1)  QVQLLESGGGLVQPGGSLRLSCAASGFRLTDEDMSWVRQAPGKGLEWVSTIATRDGSTYYADSVKGRFTI
Clone 29   (1)  QVQLLESGGGLVQPGGSLRLSCAASGYNVIYEDMGWVRQAPGKGLEWVSGIDVPSGSTYYADSVKGRFTI
Clone 33   (1)  QVQLLESGGGLVQPGGSLRLSCAASGDMFSYDDMGWVRQAPGKGLEWVSGIQNTDGSTYYADSVKGRFTI
Clone 40   (1)  QVQLLESGGGLVQPGGSLRLSCAASGDTINPEDMGWVRQAPGKGLEWVSAIEAQSGSTYYADSVKGRFTI
Clone 56   (1)  QVQLLESGGGLVQPGGSLRLSCAASGFTVTDHDMGWVRQAPGKGLEWVSSITVGNGSTYYADSVKGRFTI
Clone 60   (1)  QVQLLESGGGLVQPGGSLRLSCAASGYMFSADVMSWVRQAPGKGLEWVSGIWIPDGSTYYADSVKGRFTI
Clone 86   (1)  QVQLLESGGGLVQPGGSLRLSCAASGDMLSAQDMGWVRQAPGKGLEWVSGIDSDDGSTYYADSVKGRFTI
Consensus  (1)  QVQLLESGGGLVQPGGSLRLSCAASGYXVSXDDMSWVRQAPGKGLEWVSAIXXXDGSTYYADSVKGRFTI
                                              CDR1                   CDR2

Clone 1    (71) SRDNSKNTLYLQMNSLRAEDTAVYYCAGEPLDAEDLWYWGQGTLVTVSS
Clone 3    (71) SRDNSKNTLYLQMNSLRAEDTAVYYCAIDHGEEHKELYSWGQGTLVTVSS
Clone 9    (71) SRDNSKNTLYLQMNSLRAEDTAVYYCAGEVEKSSQSMFFWGQGTLVTVSS
Clone 10   (71) SRDNSKNTLYLQMNSLRAEDTAVYYCATAFTSHEAEVHSWGQGTLVTVSS
Clone 11   (71) SRDNSKNTLYLQMNSLRAEDTAVYYCARDPYNEDDVSYWGQGTLVTVSS
Clone 17   (71) SRDNSKNTLYLQMNSLRAEDTAVYYCATDSSWENDLWYWGQGTLVTVSS
Clone 23   (71) SRDNSKNTLYLQMNSLRAEDTAVYYCAGLRDQLYGNEQLAFWGQGTLVTVSS
Clone 29   (71) SRDNSKNTLYLQMNSLRAEDTAVYYCAAVVGQDWFQAEPSEMYYWGQGTLVTVSS
Clone 33   (71) SRDNSKNTLYLQMNSLRAEDTAVYYCATLYDRMVGKEEQLASWGQGTLVTVSS
Clone 40   (71) SRDNSKNTLYLQMNSLRAEDTAVYYCARLTAHQEEPVAYWGQGTLVTVSS
Clone 56   (71) SRDNSKNTLYLQMNSLRAEDTAVYYCATEPLPHQEVTYWGQGTLVTVSS
Clone 60   (71) SRDNSKNTLYLQMNSLRAEDTAVYYCAALNERIASITKNMHSWGQGTLVTVSS
Clone 86   (71) SRDNSKNTLYLQMNSLRAEDTAVYYCAALWGEDVIMQDSSVCSWGQGTLVTVSS
Consensus  (71) SRDNSKNTLYLQMNSLRAEDTAVYYCAXXXXXXXXXXXXXLXYWGQGTLVTVSS
                                                CDR3
```

(TetraTE), a penta-specific T cell engager molecule (PentaTE), a chimeric antigen receptor, a full antibody, an antibody-drug conjugate (ADC) molecule, a targeted delivery construct, or a labeling construct.

13 Claims, 6 Drawing Sheets

Specification includes a Sequence Listing.

(58) Field of Classification Search
CPC .......... C07K 2317/622; C07K 2317/74; C07K 16/283; C07K 2317/73; A61K 47/6849; A61K 39/00; A61K 2039/505; A61P 35/00
See application file for complete search history.

(56) References Cited

U.S. PATENT DOCUMENTS

| | | | | |
|---|---|---|---|---|
| 10,358,492 | B2 | 7/2019 | Bakker et al. | |
| 11,098,100 | B2 | 8/2021 | Vallera et al. | |
| 11,098,101 | B2 | 8/2021 | Vallera et al. | |
| 2006/0104971 | A1 | 5/2006 | Garber et al. | |
| 2006/0134102 | A1 | 6/2006 | Lepage et al. | |
| 2009/0215119 | A1 | 8/2009 | Ladner | |
| 2014/0072581 | A1 | 3/2014 | Dixit et al. | |
| 2014/0120096 | A1 * | 5/2014 | Bakker et al. | C07K 16/28 424/136.1 |
| 2014/0242025 | A1 | 8/2014 | Wong et al. | |
| 2014/0378664 | A1 | 12/2014 | Suh et al. | |
| 2015/0125386 | A1 | 5/2015 | Hansen et al. | |
| 2015/0374790 | A1 | 12/2015 | Liu et al. | |
| 2017/0368169 | A1 | 12/2017 | Loew et al. | |
| 2018/0282386 | A1 | 10/2018 | Vallera et al. | |
| 2020/0087369 | A1 | 3/2020 | Vallera et al. | |
| 2020/0148737 | A1 | 5/2020 | Vallera et al. | |
| 2021/0395326 | A1 | 12/2021 | Vallera et al. | |

FOREIGN PATENT DOCUMENTS

| | | | |
|---|---|---|---|
| EP | 3457139 | 3/2019 | |
| JP | 2010-500967 | 1/2010 | |
| JP | 2010-517048 | 5/2010 | |
| JP | 2012-100677 | 5/2012 | |
| JP | 2013-513370 | 4/2013 | |
| JP | 2013-535187 | 9/2013 | |
| JP | 2014-507150 | 3/2014 | |
| JP | 2014-518064 | 7/2014 | |
| RU | 2014100350 | 7/2015 | |
| WO | 2005/089788 | 9/2005 | |
| WO | 2006/099141 | 9/2006 | |
| WO | 2008/011157 | 1/2008 | |
| WO | 2008/092164 | 7/2008 | |
| WO | 2009/029601 | 3/2009 | |
| WO | 2009/051974 | 4/2009 | |
| WO | WO-2011047442 A1 * | 4/2011 | A61K 47/48546 |
| WO | 2011/070109 | 6/2011 | |
| WO | 2012/006490 | 1/2012 | |
| WO | 2012/040323 | 3/2012 | |
| WO | 2012/113266 | 8/2012 | |
| WO | 2012/167143 | 12/2012 | |
| WO | 2012/175222 | 12/2012 | |
| WO | 2013/039883 | 3/2013 | |
| WO | 2013/163427 | 10/2013 | |
| WO | 2014/138306 | 9/2014 | |
| WO | 2015/090229 | 6/2015 | |
| WO | 2017/062604 | 4/2017 | |
| WO | WO 2018/202649 A1 | 11/2018 | |
| WO | 2019/035938 | 2/2019 | |
| WO | WO 2019/108065 A1 | 6/2019 | |
| WO | WO 2019/118918 A1 | 6/2019 | |
| WO | 2019/139888 | 7/2019 | |

OTHER PUBLICATIONS

Hoey et al. Exp Biol Med. Dec. 2019;244(17):1568-1576. PMID: 31594404 (Year: 2019).*

Alderson, "Clinical cancer therapy by NK cells via antibody-dependent cell-mediated cytotoxicity" 2011 Journal of biomedicine & biotechnology, 2011:379123.

Almagro et al., "Humanization of Antibodies," Frontiers in Bioscience, 2008; 13:1619-1633.

American Type Culture Collection, "ATCC HL-60, CCI-240, a CD33+ human acute promyelocytic leukemia cell line," organism: *Homo sapiens*, human; [online] Manassas, VA [retrieved on Apr. 4, 2019 from the Internet: https://www.atcc.org/~/ps/CCL-240.ashx. 3 pgs.

American Type Culture Collection, "HT29, ATCC HTB38," organism: *Homo sapiens*, human; [online] Manassas, VA [retrieved on Apr. 4, 2019] from the Internet: https://www.ncbi.nlm.nih.gov/nuccore/EF561291.1. 3 pgs.

Amet, "Insertion of the Designed Helical Linker Led to Increased Expression of TF-based fusion proteins" Mar. 2009 Pharm. Res., 26(3):523-528.

Artis, "The biology of innate lymphoid cells" 2015 Nature, 517:293-301.

Bachanova, "Clearance of acute myeloid leukemia by haploidentical natural killer cells is improved using IL-2 diphtheria toxin fusion protein" 2014 Blood, 123:3855-63.

Badolato, "Interleukin-15 (IL-15) induces IL-8 and monocyte chemotactic protein 1 production in human monocytes" 1997 Blood, 90: 2804-9.

Baeuerle, "EpCAM (CD326) finding its role in cancer" 2007 Br J Cancer, 96(3):417-23.

Bargou, "Tumor regression in cancer patients by very low doses of a T cell-engaging antibody" 2008 Science, 321(5891):974-7.

Barrett, "Toxicity management for patients receiving novel T-cell engaging therapies" 2014 Curr Opin Pediatr., 26(1):43-9.

Basak, "Interleukin 15 augments antitumor activity of cytokine gene-modified melanoma cell vaccines in a murine model" 2008 Oncol Rep., 19(5):1173-9.

Batra et al., "Recombinant anti-erbB2 immunotoxins containing Pseudomonas exotoxin", Proc. Natl. Acad. Sci. USA, vol. 89, Jul. 1992, pp. 5867-5871.

Becknell, "Interleukin-2, interleukin-15, and their roles in human natural killer cells" 2005 Adv Immunol., 86: 209-39.

Behar et al., "Isolation and characterization of anti-FcyRIII (CD16) llama single-domain antibodies that activate natural killer cells", Protein Engineering, Design & Selection, vol. 21, No. 1, 2008, pp. 1-10.

Bell, "Sustained in vivo signaling by long-lived IL-2 induces prolonged increases of regulatory T cells" 2015 J Autoimmun., 56:66-80.

Berger, "Safety and immunologic effects of IL-15 administration in nonhuman primates" 2009 Blood, (12):2417-2426.

Bezan, "Systemic effect of catumaxomab in a patient with metastasized colorectal cancer: a case report" 2013 BMC Cancer, 13:618. doi:10.1186/1471-2407-13-618.

Budagian, "IL-15/IL-15 receptor biology: a guided tour through an expanding universe" 2006 Cytokine Growth Factor Rev., 17: 259-80.

Budagian, "Reverse signaling through membrane-bound interleukin-15" 2004 J Biol Chem., 279: 42192-2.

Caligiuri, "Functional consequences of interleukin 2 receptor expression on resting human lymphocytes. Identification of a novel natural killer cell subset with high affinity receptors" 1990 J Exp Med., 171(5):1509-26.

Carson, "Interleukin (IL) 15 is a novel cytokine that activates human natural killer cells via components of the IL-2 receptor" 1994 J Exp Med., 180(4):1395-403.

Chen et al., "Enhancement and destruction of antibody function by somatic mutation: unequal occurrence is controlled by V gene combinatorial associations," EMBO Journal, 1995, 14(12): 2784-2794.

Colman, "Effects of amino acid sequence changes on antibody-antigen interactions," Research in Immunology, 1994, 145:33-36.

(56) References Cited

OTHER PUBLICATIONS

Conlon, "Redistribution, hyperproliferation, activation of natural killer cells and CD8 T cells, and cytokine production during first-in-human clinical trial of recombinant human interleukin-15 in patients with cancer" 2015 J Clin Oncol., 33(1):74-82.
Connor, "Ex vivo evaluation of anti-EpCAM immunocytokine huKS-IL2 in ovarian cancer" 2004 J Immunother., 27(3):211-9.
Cooper, "Human natural killer cells: a unique innate immunoregulatory role for the CD56(bright) subset" 2001 Blood, 97(10):3146-51.
Ensinger, "EpCAM overexpression in thyroid carcinomas: a histopathological study of 121 cases" 2006 J Immunother., 29(5):569-73.
European Search Report for European Patent Application No. 16854310.6, issued Jul. 5, 2019. 14 pgs.
Fehniger, "Differential cytokine and chemokine gene expression by human NK cells following activation with IL-18 or L-15 in combination with IL-12: implications for the innate immune response" 1999 J Immunol., 162(8):4511-20.
Fehniger, "Fatal leukemia in interleukin 15 transgenic mice follows early expansions in natural killer and memory phenotype CD8+ T cells" 2001 J Exp Med., (193): 219-31.
Felices et al., "Generation of BiKEs and TriKEs to improve NK cell-mediated targeting of tumor cells," Methods Mol Biol., 2016; 1441:333-346.
Felices, "CD16-IL 15-CD33 Trispecific Killer Engager (TrikE) induces NK cell expansion, persistence, and myeloid plast antigen specific killing." May 2016 The Journal of Immunology, 196(1 Supplement):75.8.
Finco, "Cytokine release assays: current practices and future directions" 2014 Cytokine, 66(2):143-55. doi: 10.1016/j. cyto.2013.12.009. Epub Jan. 10, 2014. Review.
Finney, "Activation of resting human primary T cells with chimeric receptors: costimulation from CD28, inducible costimulator, CD134, and CD137 in series with signals from the TCR zeta chain" 2004 J Immunol., 172(1):104-13.
Fogh, "One hundred and twenty-seven cultured human tumor cell lines producing tumors in nude mice" 1977 J Natl Cancer Inst., 59(1):221-6.
Foley, "NK cell education after allogeneic transplantation: dissociation between recovery of cytokine-producing and cytotoxic functions" 2011 Blood, 118:2784-92.
Foley, "The biology of NK cells and their receptors affects clinical outcomes after hematopoietic cell transplantation (HCT)" 2014 Immunol Rev., 258:45-63.
Gastl, "Ep-CAM overexpression in breast cancer as a predictor of survival" 2000 Lancet, 356(9246):1981-2.
Gleason, "Bispecific and Trispecific Killer Cell Engagers Directly Activate Human NK Cells through CD16 Signaling and Induce Cytotoxicity and Cytokine Production" Dec. 2012 Molecular Cancer Therapeutics, 11(12):2674-2684.
Gleason, "CD16xCD33 bispecific killer cell engager (BiKE) activates NK cells against primary MDS and MDSC CD33+ targets" 2014 Blood, (19):3016-26.
Gleason, "The Functional Role of the Activating Receptors Tim-3 and Cd16 in Human Natural Killer (NK) Cell Biology" dissertation University of Minnesota, Sep. 2012. 199 pages.
Grupp, "Chimeric antigen receptor-modified T cells for acute lymphoid leukemia" 2013 N Engl J Med., 368(16):1509-18.
Gutzmer, "A tumor-associated glycoprotein that blocks MHC class Il-dependent antigen presentation by dendritic cells" 2004 J Immunol., 173(2):1023-32.
Heiss, "The trifunctional antibody catumaxomab for the treatment of malignant ascites due to epithelial cancer: Results of a prospective randomized phase II/III trial" 2010 Int J Cancer, 127(9):2209-21.
Hodge, "Interleukin-15 enhances proteasomal degradation of bid in normal lymphocytes: implications for large granular lymphocyte leukemias" 2009 Cancer Res., 69(9):3986-94.
Hoseini et al., "Acute myeloid leukemia targets for bispecific antibodies", Blood Cancer Journal, 7, e522, 2017, pp. 1-12.
Huntington, "IL-15 trans-presentation promotes human NK cell development and differentiation in vivo" 2009 J Exp Med., 206(1):25-34.
Imai, "Chimeric receptors with 4-1BB signaling capacity provoke potent cytotoxicity against acute lymphoblastic eukemia" 2004 Leukemia, 18(4):676-84.
International Preliminary Report on Patentability from PCT Application No. PCT/US2016/055722, dated Apr. 19, 2018, 8 pages.
Japanese Office Action (English Translation) mailed Oct. 1, 2024; Japanese Patent Application No. JP2022-522867; 10 pages.
Yang et al., "Advances of immune cells associated with ADCC predicting the anti-tumor effect of monoclonal antibody" Chinese Journal of Cancer Prevention and Treatment. Jan. 14, 2018; English Abstract only. 2 pages.
Chinese Office Action (English Translation) mailed Aug. 29, 2024, Chinese Patent Application No. 202080087719.7; 14 pages.
International Preliminary Report on Patentability from PCT Application No. PCT/US2020/050851, dated Mar. 31, 2022, 7 pages.
International Preliminary Report on Patentability from PCT Application No. PCT/US2020/055468, dated Apr. 28, 2022, 7 pages.
International Search Report and Written Opinion from PCT Application No. PCT/US2016/055722, dated Feb. 17, 2017, 12 pages.
International Search Report and Written Opinion from PCT Application No. PCT/US2020/050851, dated Jan. 5, 2021, 10 pages.
International Search Report and Written Opinion from PCT Application No. PCT/US2020/055468, dated Mar. 11, 2021, 11 pages.
Jakobisiak, "Interleukin 15 as a promising candidate for tumor immunotherapy" 2011 Cytokine Growth Factor Rev., 22: 99-108.
Khawam, "Human renal cancer cells express a novel membrane-bound interleukin-15 that induces, in response to the soluble interleukin-15 receptor alpha chain, epithelial-to-mesenchymal transition" 2009 Cancer Res., 69(4):1561-9.
King, "Phase I clinical trial of the immunocytokine EMD 273063 in melanoma patients" 2004 J Clin Oncol., 22 (22):4463-73.
Klein, "Surface IgM-kappa specificity on a Burkitt lymphoma cell in vivo and in derived culture lines" 1968 Cancer Res., 28(7):1300-10.
Ko, "Safety, pharmacokinetics, and biological pharmacodynamics of the immunocytokine EMD 273066 (huKS-IL2): results of a phase I trial in patients with prostate cancer" 2004 J Immunother., 27(3):232-9.
Kuniyasu, "Interleukin-15 expression is associated with malignant potential in colon cancer cells" 2001 Pathobiology, (69):86-95.
Kuniyasu, "Production of interleukin 15 by human colon cancer cells is associated with induction of mucosal hyperplasia, angiogenesis, and metastasis" 2003 Clin Cancer Res., 9(13):4802-10.
Lanier, "Functional and biochemical analysis of CD16 antigen on natural killer cells and granulocytes" 1988 J Immunol., 141: 3478-85.
Lanier, "Natural killer cell receptor signaling" 2003 Curr Opin Immunol., (3):308-14.
Lanier, "The relationship of CD16 (Leu-11) and Leu-19 (NKH-1) antigen expression on human peripheral blood NK cells and cytotoxic T lymphocytes" 1986 J Immunol., 136(12):4480-6.
Lin, "The role of shared receptor motifs and common Stat proteins in the generation of cytokine pleiotropy and redundancy by IL-2, IL-4, IL-7, IL-13, and IL-15" 1995 Immunity, 2: 331-9.
Liu et al., "Development of Effective Therapeutics Targeting HER3 for Cancer Treatment", Biological Procedures Online, 21, 2019, 10 pages.
Ma, "Myelodysplastic syndromes: incidence and survival in the United States" 2007 Cancer, (8):1536-1542.
Maretzky, "A transforming Src mutant increases the bioavailability of EGFR ligands via stimulation of the cell-surface metalloproteinase ADAM17" 2011 Oncogene, (5): 611-8.
McCall, "Isolation and characterization of an anti-CD16 single-chain Fv fragment and construction of an anti-HER2/ neu/anti-CD16 bispecific scFv that triggers CD16-dependent tumor cytolysis" 1999 Mol Immunol., (7): 433-445.
McCormick, "Immunization with an Interferon-g-gp120 Fusion Protein Induces Enhanced Immune Responses to Human Immunodeficiency Virus gp120" Nov. 2001 J. Infectious Dis., 184:1423-30.

(56) References Cited

OTHER PUBLICATIONS

Miller, "Successful adoptive transfer and in vivo expansion of human haploidentical NK cells in patients with cancer" 2005 Blood, 105:3051-7.
Miller, "Trispecific Killer Engagers (TrikEs) that contain IL-15 to make NK cells antigen specific and to sustain their persistence and expansion" Dec. 2015 Blood, pp. 1-4.
Miller, "Therapeutic applications: natural killer cells in the clinic," Hematology Am Soc Hematol Educ Program. 2013; 2013(1):247-253.
Miller, "Expansion and homing of adoptively transferred human natural killer cells in immunodeficient mice varies with product preparation and in vivo cytokine administration: implications for clinical therapy" 2014 Biol Blood Marrow Transplant, 20:1252-7.
Mishra, "Molecular pathways: Interleukin-15 signaling in health and cancer" 2014 Clin Cancer Res., 20: 2044-50.
Munger, "Studies evaluating the antitumor activity and toxicity of interleukin-15, a new T cell growth factor: comparison with interleukin-2" 1995 Cell Immunol., 165(2):289-93.
Munz, "The carcinoma-associated antigen EpCAM upregulates c-myc and induces cell proliferation" 2004 Oncogene, 23(34):5748-58.
Munz, "The emerging role of EpCAM in cancer and stem cell signaling" 2009 Cancer Res., 69(14):5627-9.
National Center for Biotechnology Information, National Library of Medicine, National Institutes of Health, Accession No. EF5612921, " Lama glama clone C21 immunoglobulin heavy chain variable region mRNA, partial cds," [online]. Bethesda, MD [retrieved on Apr. 4, 2019]. Retrieved from the Internet: https://www.ncbi.nlm.nih.gov/nuccore/EF561291.1; 3 pgs.
NCCN. "NCCN Clinical Practice Guidelines in Oncology (NCCN Guidelines) Myelodysplastic Syndromes Version 2. 2014" 2013.
Ochoa, "Interleukin-15 in gene therapy of cancer" 2013 Curr Gene Ther.,13: 15-30.
Office Action and Search Report, dated Sep. 8, 2020, for Japanese Patent Application No. 2018-517586, translated into English, 5 pages.
Office Action and Search Report, dated Nov. 3, 2020, for Russian Patent Application No. 2018116565, Including English translation, 20 pages.
Osenga, "A phase I clinical trial of the hu14.18-IL2 (EMD 273063) as a treatment for children with refractory or recurrent neuroblastoma and melanoma: a study of the Children's Oncology Group" 2006 Clin Cancer Res., 12(6):1750-9.
Papadakis, "TL1A synergizes with IL-12 and IL-18 to enhance IFN-gamma production in human T cells and NK cells" 2004 J Immunol., 172(11):7002-7.
Petrelli, "Regression of liver metastases after treatment with intraperitoneal catumaxomab for malignant ascites due to breast cancer" 2013 Target Oncol., 8(4):291-4. doi:10.1007/s11523-012-0240-y.
Pinz, "Preclinical targeting of human T cell malignancies using CD4-specific chimeric antigen receptor (CAR)-engineered T cells" 2015 Leukemia, 30(3):701-7. doi: 10.1038/leu.2015.311, Epub Nov. 3, 2015.
Ranson, "IL-15 is an essential mediator of peripheral NK-cell homeostasis" 2003 Blood, 101(12):4887-93.
Richards, "Anti-tumour effects of a specific anti-ADAM17 antibody in an ovarian cancer model in vivo" 2012 PLoS One, (7):e40597.
Rudikoff et al. "Single amino acid substitution altering antigen-binding specificity," Proc. Natl. Acad. Sci. USA, 1982, 79(6): 1979-1983.
Russian Office Action, dated Feb. 25, 2021, for Russian patent application No. 2018116565, 5 pages.
Schmohl, "Enhanced ADCC and NK Cell Activation of an Anticarcinoma Bispecific Antibody by Genetic Insertion of a Modified IL-15 Cross-linker" Jul. 2016 Molecular Therapy, 24(7):1312-22. doi: 10.1038/mt.2016.88.
Schmohl, "Heterodimeric bispecific single chain variable fragments (scFv) killer engagers (BiKEs) enhance NK-cell activity against CD133+ colorectal cancer cells" Jun. 2016 Target Oncol., 11(3):353-361.
Schmohl, "Improvement in ADCC and NK cell activation of an anti-carcinoma bispecific antibody by genetic insertion of a modified IL-15 cross-linker" 2016 Oncol. Res. Treatm., 39:280-280.
Seimetz, "Development and approval of the trifunctional antibody catumaxomab (anti-EpCAM x anti-CD3) as a targeted cancer immunotherapy" 2010 Cancer Treat Rev., 36(6):458-67. doi: 10.1016/j.ctrv.2010.03.001.
Shanmugham, "IL-15 an immunoregulatory and anti-cancer cytokine. Recent advances" 2006 J Exp Clin Cancer Res., 25:529-36.
Singer, "Effective elimination of acute myeloid leukemic cells by recombinant bispecific antibody derivatives directed against CD33 and CD16" Jul.-Aug. 2010 J Immunother., 33:599-610 (2010).
Spizzo, "High Ep-CAM expression is associated with poor prognosis in node-positive breast cancer" 2004 Breast Cancer Res Treat., 86(3):207-13.
Steel, "Interleukin-15 biology and its therapeutic implications in cancer" 2012 Trends Pharmacol Sci., 33: 35-41.
Arvindam et al., CD16-IL15-CLEC12A Trispecific Killer Engager (TrikE) Drives NK Cell Expansion, Activation, and Antigen Specific Killing of Cancer Stem Cells in Acute Myeloid Leukemia. *Blood* 132, 1454 (2018).
Arvindam et al., A trispecific killer engager molecule against CLEC12A effectively induces NK-cell mediated killing of AML cells. *Leukemia* 35, 1586-1596 (2021).
Phung et al., Bi-specific and Tri-specific NK Cell Engagers: The New Avenue of Targeted NK Cell Immunotherapy. Mol Diagn Ther 25, 577-592 (2021).
Extended European Search Report mailed Oct. 9, 2023, European Patent Application No. 20877981.9; 12 pages.
Stein, "Novel conjugates of single-chain Fv antibody fragments specific for stem cell antigen CD123 mediate potent death of acute myeloid leukaemia cells" 2010 Br J Haematol., 148;879-885.
Strohlein, "Immunotherapy of peritoneal carcinomatosis with the antibody catumaxomab in colon, gastric, or pancreatic cancer: an open-label, multicenter, phase I/II trial" 2011 Onkologie., 34(3):101-8. doi: 10.1159/000324667.
Tatusova et al., "BLAST 2 SEQUENCES, a new tool for comparing protein and nucleotide sequences", FEMS Microbiology Letters, 174, 1999, pp. 247-250.
Trentin, "Interleukin-15 promotes the growth of leukemic cells of patients with B-cell chronic lymphoproliferative disorders" 1996 Blood, 87(8):3327-35.
Trzpis, "Epithelial cell adhesion molecule: more than a carcinoma marker and adhesion molecule" 2007 Am J Pathol., 171(2):386-95.
University of Minnesota, Arvindam et al., "CD16-IL15-CLEC12A Trispecific Killer Engager (TrikE) Drives NK Cell Expansion, Activation, and Antigen Specific Killing of Cancer Stem Cells in Acute Myeloid Leukemia" Poster, presented at ASH 2018—60th American Society of Hematology Annual Meeting and Exposition, San Diego, CA; Dec. 1-4, 2018; 1 page.
University of Minnesota, Felices et al. "CD16-IL15-CLEC12A Tri-specific Killer Engager (TriKE) drives NK cell expansion, persistence, and antigen specific killing of Cancer Stem Cells in MDS and AML" Poster, presented at the 17th meeting for the Society for Natural Immunity, San Antonio, TX; May 28-Jun. 1, 2018; 1 page.
Vallera, "IL-15 Trispecific Killer Engagers (TrikEs) Make Natural Killer Cells Specific to CD33+ Targets While Also Inducing Persistence, In Vivo Expansion, and Enhanced Function" Feb. 2016 Clin Cancer Res., 22(14):3440-3450.
Vallera, "Molecular modification of a recombinant, bivalent anti-human CD3 immunotoxin (Bic3) results in reduced in vivo toxicity in mice" 2005 Leuk Res., 29:331-41.
Vallera, "Genetic alteration of a bispecific ligand-directed toxin targeting human CD19 and CD22 receptors resulting In improved efficacy against systemic B cell malignancy" 2009 Leuk Res., 33:1233-42.
Vallera, "Heterodimeric bispecific single-chain variable-fragment antibodies against EpCAM and CD16 induce effective antibody-

(56) References Cited

OTHER PUBLICATIONS dependent cellular cytotoxicity against human carcinoma cells" 2013 Cancer Biother Radiopharm., (4):274-82.
Verneris, "Mismatch is Associated with Worse Outcomes after Unrelated Donor Reduced-Intensity Conditioning Hematopoietic Cell Transplantation: An Analysis from the Center for International Blood and Marrow Transplant Research" 2015 Biol Blood Marrow Transplant, 21:1783-9.
Vincke, "General strategy to humanize a camelid single-domain antibody and identification of a universal humanized hanobody scaffold" 2009 J Biol Chem., 284(5):3273-3284.
Waldmann, "Interleukin-15 in the treatment of cancer" 2014 Expert Rev Clin Immunol., 10:1689-701.
Waldron, "Targeting tumor-initiating cancer cells with dCD133KDEL shows impressive tumor reductions in a kenotransplant model of human head and neck cancer" 2011 Mol Cancer Ther., 10:1829-38.
Weskamp, "Pathological neovascularization is reduced by inactivation of ADAM17 in endothelial cells but not in bericytes" Mar. 2010 Circ Res., (5): 932-40.
Wiernik, "Targeting natural killer cells to acute myeloid leukemia in vitro with a CD16 x 33 bispecific killer cell engager and ADAM17 inhibition" 2013 Clin Cancer Res., (14): 3844-55.
Worsham et al., "Fine-mapping loss of gene architecture at the CDKN2B (p15INK4b), CDKN2A (p14ARF, p16INK4a), and MTAP genes in head and neck squamous cell carcinoma", Arch Otolaryngol Head Neck Surg., vol. 132 (4), Apr. 2006, pp. 409-415.
Wu, "Expression of interleukin 15 in primary adult acute lymphoblastic leukemia" 2010 Cancer, (116):387-92.
Yamamoto, "Circulating CD4+CD25+ regulatory T cells in patients with pancreatic cancer" 2012 Pancreas, 41(3):409-15. doi: 10.1097/MPA.0b013e3182373a66.
Yokoyama, "Immune functions encoded by the natural killer gene complex" 2003 Nat Rev Immunol., (4):304-16.
Zambello, "Interleukin-15 triggers the proliferation and cytotoxicity of granular lymphocytes in patients with lymphoproliferative disease of granular lymphocytes" 1997 Blood, (89): 201-11.
Konning et al., Camelid and shark single domain antibodies: structural features and therapeutic potential. Curr Opin Struct Biol 45, 10-16 (2017).
Muyldermans, Nanobodies: natural single-domain antibodies. Annu Rev Biochem 82, 775-797 (2013).
Canadian Patent Application No. 3,158,111, filed Apr. 14, 2022; Office Action issued Mar. 2, 2026, 5 pages.

* cited by examiner

FIG. 1

| | | |
|---|---|---|
| Clone 1 | (1) | QVQLQESGGGLVQPGGSLRLSCAASGDRFSNDVMAWVRQAPGKGLEWVSAIVTQDGSTYYADSVKGRFTI |
| Clone 3 | (1) | QVQLLESGGGLVQPGGSLRLSCAASGVRVSAQFMSWVRQAPGKGLEWVSSIYKKNGSTYYADSVKGRFTI |
| Clone 9 | (1) | QVQLLESGGGLVQPGGSLRLSCAASGYSITDQDMSWVRQAPGKGLEWVSGILATSGSTYYADSVKGRFTI |
| Clone 10 | (1) | QVQLLESGGGLVQPGGSLRLSCAASGVNVTADDMSWVRQAPGKGLEWVSTIDGGDGSTYYADSVKGRFTI |
| Clone 11 | (1) | QVQLLESGGGLVQPGGSLRLSCAASGYRLSNDIMAWVRQAPGKGLEWVSAIVDTDGSTYYADSVKGRFTI |
| Clone 17 | (1) | QVQLLESGGGLVQPGGSLRLSCAASGFRFIAQDMSWVRQATGKGLEWVSTIATNDGSTYYADSVKGRFTI |
| Clone 23 | (1) | QVQLLESGGGLVQPGGSLRLSCAASGFRLTDEDMSWVRQAPGKGLEWVSTIATRDGSTYYADSVKGRFTI |
| Clone 29 | (1) | QVQLLESGGGLVQPGGSLRLSCAASGYNVIYEDMGWVRQAPGKGLEWVSGIDVPSGSTYYADSVKGRFTI |
| Clone 33 | (1) | QVQLLESGGGLVQPGGSLRLSCAASGDMFSYDDMGWVRQAPGKGLEWVSGIQNTDGSTYYADSVKGRFTI |
| Clone 40 | (1) | QVQLLESGGGLVQPGGSLRLSCAASGDTINPEDMGWVRQAPGKGLEWVSAIEAQSGSTYYADSVKGRFTI |
| Clone 56 | (1) | QVQLLESGGGLVQPGGSLRLSCAASGFTVTDHDMGWVRQAPGKGLEWVSSITVGNGSTYYADSVKGRFTI |
| Clone 60 | (1) | QVQLLESGGGLVQPGGSLRLSCAASGYMFSADVMSWVRQAPGKGLEWVSGIWIPDGSTYYADSVKGRFTI |
| Clone 86 | (1) | QVQLLESGGGLVQPGGSLRLSCAASGDMLSAQDMGWVRQAPGKGLEWVSGIDSDDGSTYYADSVKGRFTI |
| Consensus | (1) | QVQLLESGGGLVQPGGSLRLSCAASGYXVSXDDMSWVRQAPGKGLEWVSAIXXXDGSTYYADSVKGRFTI |

CDR1 CDR2

| | | |
|---|---|---|
| Clone 1 | (71) | SRDNSKNTLYLQMNSLRAEDTAVYYCAGEPLDAEDLWYWGQGTLVTVSS |
| Clone 3 | (71) | SRDNSKNTLYLQMNSLRAEDTAVYYCAIDHGEEHKELYSWGQGTLVTVSS |
| Clone 9 | (71) | SRDNSKNTLYLQMNSLRAEDTAVYYCAGEVEKSSQSMPFWGQGTLVTVSS |
| Clone 10 | (71) | SRDNSKNTLYLQMNSLRAEDTAVYYCATAFTSHEAEVHSWGQGTLVTVSS |
| Clone 11 | (71) | SRDNSKNTLYLQMNSLRAEDTAVYYCARDPYNEDDVSYWGQGTLVTVSS |
| Clone 17 | (71) | SRDNSKNTLYLQMNSLRAEDTAVYYCATDSSWENDLWYWGQGTLVTVSS |
| Clone 23 | (71) | SRDNSKNTLYLQMNSLRAEDTAVYYCAGLRDQLYGNEQLAFWGQGTLVTVSS |
| Clone 29 | (71) | SRDNSKNTLYLQMNSLRAEDTAVYYCAAVVGQDWFQAEPSEMYYWGQGTLVTVSS |
| Clone 33 | (71) | SRDNSKNTLYLQMNSLRAEDTAVYYCATLYDRMVGKEEQLASWGQGTLVTVSS |
| Clone 40 | (71) | SRDNSKNTLYLQMNSLRAEDTAVYYCARLTAHQEEPVAYWGQGTLVTVSS |
| Clone 56 | (71) | SRDNSKNTLYLQMNSLRAEDTAVYYCATEPLPHQEVTYWGQGTLVTVSS |
| Clone 60 | (71) | SRDNSKNTLYLQMNSLRAEDTAVYYCAALNERIASITKNMHSWGQGTLVTVSS |
| Clone 86 | (71) | SRDNSKNTLYLQMNSLRAEDTAVYYCAALWGEDVIMQDSSVGSWGQGTLVTVSS |
| Consensus | (71) | SRDNSKNTLYLQMNSLRAEDTAVYYCAXXXXXXXXXXXXLXYWGQGTLVTVSS |

CDR3

FIG. 8
(A)
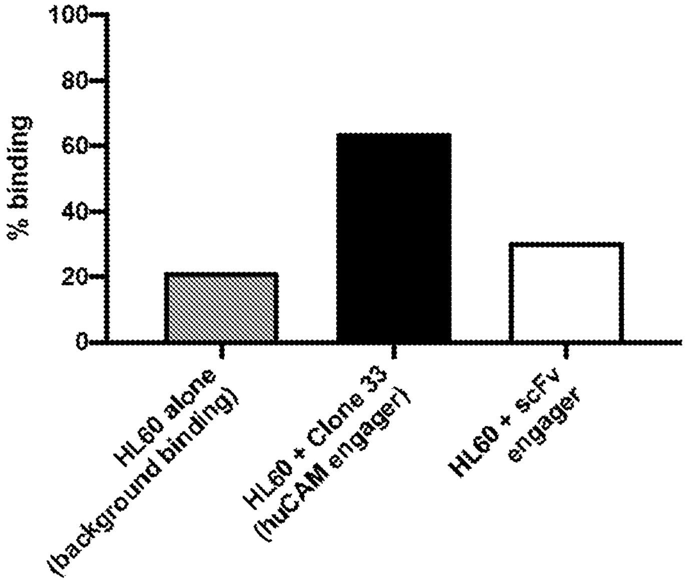
(B)
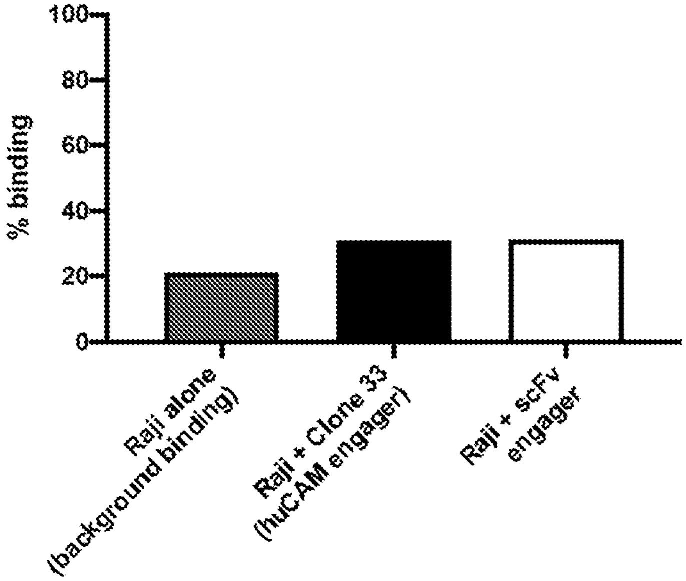

SEQUENCE LISTING

<160> NUMBER OF SEQ ID NOS: 36

<210> SEQ ID NO 1
<211> LENGTH: 119
<212> TYPE: PRT
<213> ORGANISM: Artificial
<220> FEATURE:
<223> OTHER INFORMATION: anti-CLEC12A clone 1

<400> SEQUENCE: 1

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asp Arg Phe Ser Asn Asp
            20                  25                  30

```
Val Met Ala Trp Val Arg Gln Ala Pro Gly Lys Gly Leu Glu Trp Val
        35                  40                  45

Ser Ala Ile Val Thr Gln Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Glu Pro Leu Asp Ala Glu Asp Leu Trp Tyr Trp Gly Gln Gly
            100                 105                 110

Thr Leu Val Thr Val Ser Ser
        115


<210> SEQ ID NO 2
<211> LENGTH: 120
<212> TYPE: PRT
<213> ORGANISM: Artificial
<220> FEATURE:
<223> OTHER INFORMATION: anti-CLEC12A clone 3

<400> SEQUENCE: 2

Gln Val Gln Leu Leu Glu Ser Gly Gly Gly Leu Val Gln Pro Gly Gly
1               5                   10                  15

Ser Leu Arg Leu Ser Cys Ala Ala Ser Gly Val Arg Val Ser Ala Gln
            20                  25                  30

Phe Met Ser Trp Val Arg Gln Ala Pro Gly Lys Gly Leu Glu Trp Val
        35                  40                  45

Ser Ser Ile Tyr Lys Lys Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Asp His Gly Glu Glu His Lys Glu Leu Tyr Ser Trp Gly Gln
            100                 105                 110

Gly Thr Leu Val Thr Val Ser Ser
        115                 120


<210> SEQ ID NO 3
<211> LENGTH: 120
<212> TYPE: PRT
<213> ORGANISM: Artificial
<220> FEATURE:
<223> OTHER INFORMATION: anti-CLEC12A clone 9

<400> SEQUENCE: 3

Gln Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Ile Thr Asp Gln
            20                  25                  30

Asp Met Ser Trp Val Arg Gln Ala Pro Gly Lys Gly Leu Glu Trp Val
        35                  40                  45

Ser Gly Ile Leu Ala Thr Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Gly Glu Val Glu Lys Ser Ser Gln Ser Met Pro Phe Trp Gly Gln
            100                 105                 110

Gly Thr Leu Val Thr Val Ser Ser
        115                 120


<210> SEQ ID NO 4
<211> LENGTH: 120
<212> TYPE: PRT
<213> ORGANISM: Artificial
<220> FEATURE:
<223> OTHER INFORMATION: anti-CLEC12A clone 10

<400> SEQUENCE: 4

Gln Val Gln Leu Leu Glu Ser Gly Gly Gly Leu Val Gln Pro Gly Gly
1               5                   10                  15

Ser Leu Arg Leu Ser Cys Ala Ala Ser Gly Val Asn Val Thr Ala Asp
            20                  25                  30

Asp Met Ser Trp Val Arg Gln Ala Pro Gly Lys Gly Leu Glu Trp Val
        35                  40                  45

Ser Thr Ile Asp Gly Gly Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ala Phe Thr Ser His Glu Ala Glu Val His Ser Trp Gly Gln
            100                 105                 110

Gly Thr Leu Val Thr Val Ser Ser
        115                 120


<210> SEQ ID NO 5
<211> LENGTH: 119
<212> TYPE: PRT
<213> ORGANISM: Artificial
<220> FEATURE:
<223> OTHER INFORMATION: anti-CLEC12A clone 11

<400> SEQUENCE: 5

Gln Val Gln Leu Leu Glu Ser Gly Gly Gly Leu Val Gln Pro Gly Gly
1               5                   10                  15

Ser Leu Arg Leu Ser Cys Ala Ala Ser Gly Tyr Arg Leu Ser Asn Asp
            20                  25                  30

Ile Met Ala Trp Val Arg Gln Ala Pro Gly Lys Gly Leu Glu Trp Val
        35                  40                  45

Ser Ala Ile Val Asp Thr Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Tyr Asn Glu Asp Asp Val Ser Tyr Trp Gly Gln Gly
            100                 105                 110

Thr Leu Val Thr Val Ser Ser
        115
```

<210> SEQ ID NO 6
<211> LENGTH: 119
<212> TYPE: PRT
<213> ORGANISM: Artificial
<220> FEATURE:
<223> OTHER INFORMATION: anti-CLEC12A clone 17

<400> SEQUENCE: 6

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Phe Ile Ala Gln
            20                  25                  30

Asp Met Ser Trp Val Arg Gln Ala Thr Gly Lys Gly Leu Glu Trp Val
        35                  40                  45

Ser Thr Ile Ala Thr Asn Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Ser Ser Trp Glu Asn Asp Leu Trp Tyr Trp Gly Gln Gly
            100                 105                 110

Thr Leu Val Thr Val Ser Ser
        115

<210> SEQ ID NO 7
<211> LENGTH: 122
<212> TYPE: PRT
<213> ORGANISM: Artificial
<220> FEATURE:
<223> OTHER INFORMATION: anti-CLEC12A clone 23

<400> SEQUENCE: 7

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Leu Thr Asp Glu
            20                  25                  30

Asp Met Ser Trp Val Arg Gln Ala Pro Gly Lys Gly Leu Glu Trp Val
        35                  40                  45

Ser Thr Ile Ala Thr Arg Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Leu Arg Asp Gln Leu Tyr Gly Asn Glu Gln Leu Ala Phe Trp
            100                 105                 110

Gly Gln Gly Thr Leu Val Thr Val Ser Ser
        115                 120

<210> SEQ ID NO 8
<211> LENGTH: 125
<212> TYPE: PRT
<213> ORGANISM: Artificial
<220> FEATURE:
<223> OTHER INFORMATION: anti-CLEC12A clone 29

<400> SEQUENCE: 8

Gln Val Gln Leu Leu Glu Ser Gly Gly Gly Leu Val Gln Pro Gly Gly
1               5                   10                  15

```
Ser Leu Arg Leu Ser Cys Ala Ala Ser Gly Tyr Asn Val Ile Tyr Glu
            20                  25                  30

Asp Met Gly Trp Val Arg Gln Ala Pro Gly Lys Gly Leu Glu Trp Val
        35                  40                  45

Ser Gly Ile Asp Val Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Val Val Gly Gln Asp Trp Phe Gln Ala Glu Pro Ser Glu Met
            100                 105                 110

Tyr Tyr Trp Gly Gln Gly Thr Leu Val Thr Val Ser Ser
        115                 120                 125


<210> SEQ ID NO 9
<211> LENGTH: 123
<212> TYPE: PRT
<213> ORGANISM: Artificial
<220> FEATURE:
<223> OTHER INFORMATION: anti-CLEC12A clone 33

<400> SEQUENCE: 9

Gln Val Gln Leu Leu Glu Ser Gly Gly Gly Leu Val Gln Pro Gly Gly
1               5                   10                  15

Ser Leu Arg Leu Ser Cys Ala Ala Ser Gly Asp Met Phe Ser Tyr Asp
            20                  25                  30

Asp Met Gly Trp Val Arg Gln Ala Pro Gly Lys Gly Leu Glu Trp Val
        35                  40                  45

Ser Gly Ile Gln Asn Thr Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Tyr Asp Arg Met Val Gly Lys Glu Glu Gln Leu Ala Ser
            100                 105                 110

Trp Gly Gln Gly Thr Leu Val Thr Val Ser Ser
        115                 120


<210> SEQ ID NO 10
<211> LENGTH: 120
<212> TYPE: PRT
<213> ORGANISM: Artificial
<220> FEATURE:
<223> OTHER INFORMATION: anti-CLEC12A clone 40

<400> SEQUENCE: 10

Gln Val Gln Leu Leu Glu Ser Gly Gly Gly Leu Val Gln Pro Gly Gly
1               5                   10                  15

Ser Leu Arg Leu Ser Cys Ala Ala Ser Gly Asp Thr Ile Asn Pro Glu
            20                  25                  30

Asp Met Gly Trp Val Arg Gln Ala Pro Gly Lys Gly Leu Glu Trp Val
        35                  40                  45

Ser Ala Ile Glu Ala Gln Ser Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr Ala His Gln Glu Glu Pro Val Ala Tyr Trp Gly Gln
            100                 105                 110

Gly Thr Leu Val Thr Val Ser Ser
        115                 120


<210> SEQ ID NO 11
<211> LENGTH: 119
<212> TYPE: PRT
<213> ORGANISM: Artificial
<220> FEATURE:
<223> OTHER INFORMATION: anti-CLEC12A clone 56

<400> SEQUENCE: 11

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Thr Asp His
            20                  25                  30

Asp Met Gly Trp Val Arg Gln Ala Pro Gly Lys Gly Leu Glu Trp Val
        35                  40                  45

Ser Ser Ile Thr Val Gly Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Pro Leu Pro His Gln Glu Val Thr Tyr Trp Gly Gln Gly
            100                 105                 110

Thr Leu Val Thr Val Ser Ser
        115


<210> SEQ ID NO 12
<211> LENGTH: 124
<212> TYPE: PRT
<213> ORGANISM: Artificial
<220> FEATURE:
<223> OTHER INFORMATION: anti-CLEC12A clone 60

<400> SEQUENCE: 12

Gln Val Gln Leu Leu Glu Ser Gly Gly Gly Leu Val Gln Pro Gly Gly
1               5                   10                  15

Ser Leu Arg Leu Ser Cys Ala Ala Ser Gly Tyr Met Phe Ser Ala Asp
            20                  25                  30

Val Met Ser Trp Val Arg Gln Ala Pro Gly Lys Gly Leu Glu Trp Val
        35                  40                  45

Ser Gly Ile Trp Ile Pro Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gln Leu Asn Glu Arg Ile Ala Ser Ile Thr Lys Asn Met His
            100                 105                 110
```

```
Ser Trp Gly Gln Gly Thr Leu Val Thr Val Ser Ser
        115                 120


<210> SEQ ID NO 13
<211> LENGTH: 124
<212> TYPE: PRT
<213> ORGANISM: Artificial
<220> FEATURE:
<223> OTHER INFORMATION: anti-CLEC12A clone 86

<400> SEQUENCE: 13

Gln Val Gln Leu Leu Glu Ser Gly Gly Gly Leu Val Gln Pro Gly Gly
1               5                   10                  15

Ser Leu Arg Leu Ser Cys Ala Ala Ser Gly Asp Met Leu Ser Ala Gln
            20                  25                  30

Asp Met Gly Trp Val Arg Gln Ala Pro Gly Lys Gly Leu Glu Trp Val
        35                  40                  45

Ser Gly Ile Asp Ser Asp Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Leu Trp Gly Glu Asp Val Ile Met Gln Asp Ser Ser Val Gly
            100                 105                 110

Ser Trp Gly Gln Gly Thr Leu Val Thr Val Ser Ser
        115                 120


<210> SEQ ID NO 14
<211> LENGTH: 124
<212> TYPE: PRT
<213> ORGANISM: Artificial
<220> FEATURE:
<223> OTHER INFORMATION: anti-CLEC12A clone consensus sequence
<220> FEATURE:
<221> NAME/KEY: MISC_FEATURE
<222> LOCATION: (28)..(28)
<223> OTHER INFORMATION: X= any amino acid or no amino acid
<220> FEATURE:
<221> NAME/KEY: MISC_FEATURE
<222> LOCATION: (31)..(31)
<223> OTHER INFORMATION: X= any amino acid or no amino acid
<220> FEATURE:
<221> NAME/KEY: MISC_FEATURE
<222> LOCATION: (52)..(54)
<223> OTHER INFORMATION: X= any amino acid or no amino acid
<220> FEATURE:
<221> NAME/KEY: MISC_FEATURE
<222> LOCATION: (98)..(110)
<223> OTHER INFORMATION: X= any amino acid or no amino acid
<220> FEATURE:
<221> NAME/KEY: MISC_FEATURE
<222> LOCATION: (112)..(112)
<223> OTHER INFORMATION: X= any amino acid or no amino acid

<400> SEQUENCE: 14

Gln Val Gln Leu Leu Glu Ser Gly Gly Gly Leu Val Gln Pro Gly Gly
1               5                   10                  15

Ser Leu Arg Leu Ser Cys Ala Ala Ser Gly Tyr Xaa Val Ser Xaa Asp
            20                  25                  30

Asp Met Ser Trp Val Arg Gln Ala Pro Gly Lys Gly Leu Glu Trp Val
        35                  40                  45

Ser Ala Ile Xaa Xaa Xaa Asp Gly Ser Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Xaa Xaa Xaa Xaa Xaa Xaa Xaa Xaa Xaa Xaa Xaa Xaa Xaa Leu Xaa
            100                 105                 110

Tyr Trp Gly Gln Gly Thr Leu Val Thr Val Ser Ser
        115                 120


<210> SEQ ID NO 15
<211> LENGTH: 533
<212> TYPE: PRT
<213> ORGANISM: Artificial
<220> FEATURE:
<223> OTHER INFORMATION: CLEC12A TriKE amino acid sequence

<400> SEQUENCE: 15

Met Lys Trp Val Thr Phe Ile Ser Leu Leu Phe Leu Phe Ser Ser Ala
1               5                   10                  15

Tyr Ser Gln Val Gln Leu Val Glu Ser Gly Gly Gly Leu Val Gln Pro
            20                  25                  30

Gly Gly Ser Leu Arg Leu Ser Cys Ala Ala Ser Gly Leu Thr Phe Ser
        35                  40                  45

Ser Tyr Asn Met Gly Trp Phe Arg Gln Ala Pro Gly Gln Gly Leu Glu
    50                  55                  60

Ala Val Ala Ser Ile Thr Trp Ser Gly Arg Asp Thr Phe Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Ala Asn Pro Trp Pro Val Ala Ala Pro Arg Ser Gly Thr
        115                 120                 125

Tyr Trp Gly Gln Gly Thr Leu Val Thr Val Ser Ser Ser Gly Gly Gly
    130                 135                 140

Gly Ser Gly Gly Gly Gly Ser Gly Gly Gly Gly Ser Gly Gly Gly Gly
145                 150                 155                 160

Ser Gly Asn Trp Val Asn Val Ile Ser Asp Leu Lys Lys Ile Glu Asp
                165                 170                 175

Leu Ile Gln Ser Met His Ile Asp Ala Thr Leu Tyr Thr Glu Ser Asp
            180                 185                 190

Val His Pro Ser Cys Lys Val Thr Ala Met Lys Cys Phe Leu Leu Glu
        195                 200                 205

Leu Gln Val Ile Ser Leu Glu Ser Gly Asp Ala Ser Ile His Asp Thr
    210                 215                 220

Val Glu Asn Leu Ile Ile Leu Ala Asn Asn Ser Leu Ser Ser Asn Gly
225                 230                 235                 240

Asn Val Thr Glu Ser Gly Cys Lys Glu Cys Glu Glu Leu Glu Glu Lys
                245                 250                 255

Asn Ile Lys Glu Phe Leu Gln Ser Phe Val His Ile Val Gln Met Phe
            260                 265                 270

Ile Asn Thr Ser Gly Ser Thr Ser Gly Ser Gly Lys Pro Gly Ser Gly
        275                 280                 285

Glu Gly Ser Thr Lys Gly Gln Val Gln Leu Gln Glu Ser Gly Pro Gly
    290                 295                 300
```

```
Leu Val Lys Pro Ser Glu Thr Leu Ser Leu Thr Cys Val Val Ser Gly
305                 310                 315                 320

Gly Ser Ile Ser Ser Ser Asn Trp Trp Ser Trp Val Arg Gln Pro Pro
                325                 330                 335

Gly Lys Gly Leu Glu Trp Ile Gly Glu Ile Tyr His Ser Gly Ser Pro
            340                 345                 350

Asp Tyr Asn Pro Ser Leu Lys Ser Arg Val Thr Ile Ser Val Asp Lys
        355                 360                 365

Ser Arg Asn Gln Phe Ser Leu Lys Leu Ser Ser Val Thr Ala Ala Asp
    370                 375                 380

Thr Ala Val Tyr Tyr Cys Ala Lys Val Ser Thr Gly Gly Phe Phe Asp
385                 390                 395                 400

Tyr Trp Gly Gln Gly Thr Leu Val Thr Val Ser Ser Gly Gly Gly Gly
                405                 410                 415

Ser Gly Gly Gly Gly Ser Gly Gly Gly Gly Ser Glu Ile Glu Leu Thr
            420                 425                 430

Gln Ser Pro Ser Ser Leu Ser Ala Ser Val Gly Asp Arg Val Thr Ile
        435                 440                 445

Thr Cys Arg Ala Ser Gln Ser Ile Ser Ser Tyr Leu Asn Trp Tyr Gln
    450                 455                 460

Gln Lys Pro Gly Lys Ala Pro Lys Leu Leu Ile Tyr Ala Ala Ser Ser
465                 470                 475                 480

Leu Gln Ser Gly Val Pro Ser Arg Phe Ser Gly Ser Gly Ser Gly Thr
                485                 490                 495

Asp Phe Thr Leu Thr Ile Ser Ser Leu Gln Pro Glu Asp Phe Ala Thr
            500                 505                 510

Tyr Tyr Cys Gln Gln Ser Tyr Ser Thr Pro Pro Thr Phe Gly Pro Gly
        515                 520                 525

Thr Lys Val Glu Ile
    530


<210> SEQ ID NO 16
<211> LENGTH: 357
<212> TYPE: DNA
<213> ORGANISM: Artificial
<220> FEATURE:
<223> OTHER INFORMATION: anti-CLEC12A clone 1

<400> SEQUENCE: 16

caggtgcagc tgtaggagtc tgggggaggc ttggtacagc ctggggggtc cctgcgtctc      60

tcctgtgcag cctccggaga taggtttagc aatgacgtta tggcctgggt ccgccaggct     120

ccagggaagg gtctagagtg ggtatcagcc attgttaccc aagacggtag cacatactac     180

gcagactccg tgaagggccg gttcaccatc tcccgtgaca attccaagaa cacgctgtat     240

ctgcaaatga acagcctgcg tgccgaggac accgcggtat attattgcgc gggagagcct     300

cttgatgccg aggacttgtg gtattggggt cagggaaccc tggtcaccgt ctcgagc        357


<210> SEQ ID NO 17
<211> LENGTH: 330
<212> TYPE: DNA
<213> ORGANISM: Artificial
<220> FEATURE:
<223> OTHER INFORMATION: anti-CLEC12A clone 3
```

<400> SEQUENCE: 17
caggtgcagc tgttggagtc tgggggaggc ttggtacagc ctggggggtc cctgcgtctc 60
gcttagttta tgagctgggt ccgccaggct ccagggaagg gtctagagtg ggtatcaagc 120
atttataaga aaaacggtag cacatactac gcagactccg tgaagggccg gttcaccatc 180
tcccgtgaca attccaagaa cacgctgtat ctgcaaatga acagcctgcg tgccgaggac 240
accgcggtat attattgcgc gattgatcat ggggaggagc acaaggagct gtactcttgg 300
ggtcagggaa ccctggtcac cgtctcgagc 330

<210> SEQ ID NO 18
<211> LENGTH: 360
<212> TYPE: DNA
<213> ORGANISM: Artificial
<220> FEATURE:
<223> OTHER INFORMATION: anti-CLEC12A clone 9

<400> SEQUENCE: 18
caggtgcagc tgttggagtc tgggggaggc ttggtacagc ctggggggtc cctgcgtctc 60
tcctgtgcag cctccggata tagcattacc gattaggata tgagctgggt ccgccaggct 120
ccagggaagg gtctagagtg ggtatcaggc attctggcca caagcggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gggagaggtt 300
gagaagagtt cccagtcgat gccgttttgg ggtcagggaa ccctggtcac cgtctcgagc 360

<210> SEQ ID NO 19
<211> LENGTH: 360
<212> TYPE: DNA
<213> ORGANISM: Artificial
<220> FEATURE:
<223> OTHER INFORMATION: anti-CLEC12A clone 10

<400> SEQUENCE: 19
caggtgcagc tgttggagtc tgggggaggc ttggtacagc ctggggggtc cctgcgtctc 60
tcctgtgcag cctccggagt taacgttacc gctgacgata tgagctgggt ccgccaggct 120
ccagggaagg gtctagagtg ggtatcaacc attgatggcg gtgacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gactgctttt 300
acgtcgcatg aggcggaggt ccactcttgg ggtcagggaa ccctggtcac cgtctcgagc 360

<210> SEQ ID NO 20
<211> LENGTH: 357
<212> TYPE: DNA
<213> ORGANISM: Artificial
<220> FEATURE:
<223> OTHER INFORMATION: anti-CLEC12A clone 11

<400> SEQUENCE: 20
caggtgcagc tgttggagtc tgggggaggc ttggtacagc ctggggggtc cctgcgtctc 60
tcctgtgcag cctccggata taggcttagc aatgacatta tggcctgggt ccgccaggct 120
ccagggaagg gtctagagtg ggtatcagcc attgtggaca cagacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gagagatcct 300
tataatgagg acgacgtcag ctattggggt cagggaaccc tggtcaccgt ctcgagc 357

<210> SEQ ID NO 21
<211> LENGTH: 357
<212> TYPE: DNA
<213> ORGANISM: Artificial
<220> FEATURE:
<223> OTHER INFORMATION: anti-CLEC12A clone 17

<400> SEQUENCE: 21
caggtgcagc tgttggagtc tgggggaggc ttggtacagc ctggggggtc cctgcgtctc 60
tcctgtgcag cctccggatt taggtttatc gcttaggata tgagctgggt ccgccaggct 120
acagggaagg gtctagagtg ggtatcaacc attgctacga atgacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gactgattcg 300
tcttgggaga acgacttgtg gtattggggt cagggaaccc tggtcaccgt ctcgagc 357

<210> SEQ ID NO 22
<211> LENGTH: 366
<212> TYPE: DNA
<213> ORGANISM: Artificial
<220> FEATURE:
<223> OTHER INFORMATION: anti-CLEC12A clone 23

<400> SEQUENCE: 22
caggtgcagc tgttggagtc tgggggaggc ttggtacagc ctggggggtc cctgcgtctc 60
tcctgtgcag cctccggatt taggcttacc gatgaggata tgagctgggt ccgccaggct 120
ccagggaagg gtctagagtg ggtatcaacc attgctacca gagacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gggacttagg 300
gatcagttgt atgggaacga gtagttggcc ttttggggtc agggaaccct ggtcaccgtc 360
tcgagc 366

<210> SEQ ID NO 23
<211> LENGTH: 375
<212> TYPE: DNA
<213> ORGANISM: Artificial
<220> FEATURE:
<223> OTHER INFORMATION: anti-CLEC12A clone 29

<400> SEQUENCE: 23
caggtgcagc tgttggagtc tgggggaggc ttggtacagc ctggggggtc cctgcgtctc 60
tcctgtgcag cctccggata taacgttatc tatgaggata tgggctgggt ccgccaggct 120
ccagggaagg gtctagagtg ggtatcaggc attgatgtcc ctagcggtag cacatactac 180
gcagactccg tgaagggccg gttcaccatc tcccgtgaca attccaagaa cacgctgtat 240
ctgcaaatga acagcctgcg tgccgaggac accgcggtat attattgcgc ggctgttgtt 300
ggtcaggatt ggttttaggc tgagccctcg gagatgtact attggggtca gggaaccctg 360
gtcaccgtct cgagc 375

<210> SEQ ID NO 24
<211> LENGTH: 369
<212> TYPE: DNA

<213> ORGANISM: Artificial
<220> FEATURE:
<223> OTHER INFORMATION: anti-CLEC12A clone 33

<400> SEQUENCE: 24
caggtgcagc tgttggagtc tggggggaggc ttggtacagc ctggggggtc cctgcgtctc 60
tcctgtgcag cctccggaga tatgtttagc tatgacgata tgggctgggt ccgccaggct 120
ccagggaagg gtctagagtg ggtatcaggc atttagaaca ctgacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gactctgtat 300
gataggatgg ttgggaagga ggagcagttg gcctcttggg gtcagggaac cctggtcacc 360
gtctcgagc 369

<210> SEQ ID NO 25
<211> LENGTH: 360
<212> TYPE: DNA
<213> ORGANISM: Artificial
<220> FEATURE:
<223> OTHER INFORMATION: anti-CLEC12A clone 40

<400> SEQUENCE: 25
caggtgcagc tgttggagtc tggggggaggc ttggtacagc ctggggggtc cctgcgtctc 60
tcctgtgcag cctccggaga taccattaac cctgaggata tgggctgggt ccgccaggct 120
ccagggaagg gtctagagtg ggtatcagcc attgaggcgc aaagcggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gagattgact 300
gctcattagg aggagccggt cgcgtattgg ggtcagggaa ccctggtcac cgtctcgagc 360

<210> SEQ ID NO 26
<211> LENGTH: 357
<212> TYPE: DNA
<213> ORGANISM: Artificial
<220> FEATURE:
<223> OTHER INFORMATION: anti-CLEC12A clone 56

<400> SEQUENCE: 26
caggtgcagc tgttggagtc tggggggaggc ttggtacagc ctggggggtc cctgcgtctc 60
tcctgtgcag cctccggatt tacggttacc gatcacgata tgggctgggt ccgccaggct 120
ccagggaagg gtctagagtg ggtatcaagc attactgtgg gaaacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gacagagcct 300
ttgccgcact aggaggtcac gtattggggt cagggaaccc tggtcaccgt ctcgagc 357

<210> SEQ ID NO 27
<211> LENGTH: 357
<212> TYPE: DNA
<213> ORGANISM: Artificial
<220> FEATURE:
<223> OTHER INFORMATION: anti-CLEC12A clone 60

<400> SEQUENCE: 27
caggtgcagc tgttggagtc tggggggaggc ttggtacagc ctggggggtc cctgcgtctc 60
tcctgtgcag cctccggatt tacggttacc gatcacgata tgggctgggt ccgccaggct 120
ccagggaagg gtctagagtg ggtatcaagc attactgtgg gaaacggtag cacatactac 180

```
gcagactccg tgaagggccg gttcaccatc tcccgtgaca attccaagaa cacgctgtat    240

ctgcaaatga acagcctgcg tgccgaggac accgcggtat attattgcgc gacagagcct    300

ttgccgcact aggaggtcac gtattggggt cagggaaccc tggtcaccgt ctcgagc       357


<210> SEQ ID NO 28
<211> LENGTH: 372
<212> TYPE: DNA
<213> ORGANISM: Artificial
<220> FEATURE:
<223> OTHER INFORMATION: anti-CLEC12A clone 86

<400> SEQUENCE: 28

caggtgcagc tgttggagtc tgggggaggc ttggtacagc ctgggggtc cctgcgtctc      60

tcctgtgcag cctccggaga tatgcttagc gcttaggata tgggctgggt ccgccaggct    120

ccagggaagg gtctagagtg ggtatcaggc attgatagcg atgacggtag cacatactac    180

gcagactccg tgaagggccg gttcaccatc tcccgtgaca attccaagaa cacgctgtat    240

ctgcaaatga acagcctgcg tgccgaggac accgcggtat attattgcgc ggcattgtgg    300

ggggaggatg tgattatgta ggactcgtcg gtggggtctt ggggtcaggg aaccctggtc    360

accgtctcga gc                                                        372


<210> SEQ ID NO 29
<211> LENGTH: 5
<212> TYPE: PRT
<213> ORGANISM: Artificial
<220> FEATURE:
<223> OTHER INFORMATION: CDR1
<220> FEATURE:
<221> NAME/KEY: MISC_FEATURE
<222> LOCATION: (1)..(1)
<223> OTHER INFORMATION: X= N, A, D, Y, or P
<220> FEATURE:
<221> NAME/KEY: MISC_FEATURE
<222> LOCATION: (2)..(2)
<223> OTHER INFORMATION: X= D, E, H, Q, or deletion
<220> FEATURE:
<221> NAME/KEY: MISC_FEATURE
<222> LOCATION: (3)..(3)
<223> OTHER INFORMATION: X= V, F, I, or D
<220> FEATURE:
<221> NAME/KEY: MISC_FEATURE
<222> LOCATION: (5)..(5)
<223> OTHER INFORMATION: X= A, S, or G

<400> SEQUENCE: 29

Xaa Xaa Xaa Met Xaa
1               5


<210> SEQ ID NO 30
<211> LENGTH: 20
<212> TYPE: PRT
<213> ORGANISM: Artificial
<220> FEATURE:
<223> OTHER INFORMATION: CDR2
<220> FEATURE:
<221> NAME/KEY: MISC_FEATURE
<222> LOCATION: (1)..(1)
<223> OTHER INFORMATION: X= A,S,T, or G
<220> FEATURE:
<221> NAME/KEY: MISC_FEATURE
<222> LOCATION: (3)..(3)
<223> OTHER INFORMATION: X= V,Y,L,D,A,E,T,W, Q, or deletion
<220> FEATURE:
<221> NAME/KEY: MISC_FEATURE
<222> LOCATION: (4)..(4)
<223> OTHER INFORMATION: X= T,K,A,G,D,V,N,I, or S
```

<220> FEATURE:
<221> NAME/KEY: MISC_FEATURE
<222> LOCATION: (5)..(5)
<223> OTHER INFORMATION: X= Q,K,T,G,N,R,P, or D
<220> FEATURE:
<221> NAME/KEY: MISC_FEATURE
<222> LOCATION: (6)..(6)
<223> OTHER INFORMATION: X= D,N, or S

<400> SEQUENCE: 30

```
Xaa Ile Xaa Xaa Xaa Xaa Gly Ser Thr Tyr Tyr Ala Asp Ser Val Lys
1               5                   10                  15

Gly Arg Phe Thr
            20
```

<210> SEQ ID NO 31
<211> LENGTH: 16
<212> TYPE: PRT
<213> ORGANISM: Artificial
<220> FEATURE:
<223> OTHER INFORMATION: CDR3
<220> FEATURE:
<221> NAME/KEY: MISC_FEATURE
<222> LOCATION: (1)..(1)
<223> OTHER INFORMATION: X= any amino acid or deletion
<220> FEATURE:
<221> NAME/KEY: MISC_FEATURE
<222> LOCATION: (2)..(2)
<223> OTHER INFORMATION: X= any amino acid or deletion
<220> FEATURE:
<221> NAME/KEY: MISC_FEATURE
<222> LOCATION: (3)..(3)
<223> OTHER INFORMATION: X= any amino acid or deletion
<220> FEATURE:
<221> NAME/KEY: MISC_FEATURE
<222> LOCATION: (4)..(4)
<223> OTHER INFORMATION: X= P,E,S,Q,R,or H
<220> FEATURE:
<221> NAME/KEY: MISC_FEATURE
<222> LOCATION: (5)..(5)
<223> OTHER INFORMATION: X= any amino acid or deletion
<220> FEATURE:
<221> NAME/KEY: MISC_FEATURE
<222> LOCATION: (6)..(6)
<223> OTHER INFORMATION: X= any amino acid or deletion
<220> FEATURE:
<221> NAME/KEY: MISC_FEATURE
<222> LOCATION: (7)..(7)
<223> OTHER INFORMATION: X= any amino acid or deletion
<220> FEATURE:
<221> NAME/KEY: MISC_FEATURE
<222> LOCATION: (8)..(8)
<223> OTHER INFORMATION: X= any amino acid or deletion
<220> FEATURE:
<221> NAME/KEY: MISC_FEATURE
<222> LOCATION: (9)..(9)
<223> OTHER INFORMATION: X= any amino acid or deletion
<220> FEATURE:
<221> NAME/KEY: MISC_FEATURE
<222> LOCATION: (10)..(10)
<223> OTHER INFORMATION: X= any amino acid or deletion
<220> FEATURE:
<221> NAME/KEY: MISC_FEATURE
<222> LOCATION: (11)..(11)
<223> OTHER INFORMATION: X= any amino acid or deletion
<220> FEATURE:
<221> NAME/KEY: MISC_FEATURE
<222> LOCATION: (12)..(12)
<223> OTHER INFORMATION: X= any amino acid or deletion
<220> FEATURE:
<221> NAME/KEY: MISC_FEATURE
<222> LOCATION: (13)..(13)
<223> OTHER INFORMATION: X= any amino acid or deletion
<220> FEATURE:
<221> NAME/KEY: MISC_FEATURE
<222> LOCATION: (14)..(14)

<223> OTHER INFORMATION: X= L,M,or V
<220> FEATURE:
<221> NAME/KEY: MISC_FEATURE
<222> LOCATION: (15)..(15)
<223> OTHER INFORMATION: X= W,Y,P,H,S,A,T, or G
<220> FEATURE:
<221> NAME/KEY: MISC_FEATURE
<222> LOCATION: (16)..(16)
<223> OTHER INFORMATION: X= Y,S, or F

<400> SEQUENCE: 31

```
Xaa Xaa Xaa Xaa Xaa Xaa Xaa Xaa Xaa Xaa Xaa Xaa Xaa Xaa Xaa Xaa
1               5                   10                  15
```

<210> SEQ ID NO 32
<211> LENGTH: 18
<212> TYPE: PRT
<213> ORGANISM: Artificial
<220> FEATURE:
<223> OTHER INFORMATION: Signal peptide

<400> SEQUENCE: 32

```
Met Lys Trp Val Thr Phe Ile Ser Leu Leu Phe Leu Phe Ser Ser Ala
1               5                   10                  15

Tyr Ser
```

<210> SEQ ID NO 33
<211> LENGTH: 13
<212> TYPE: PRT
<213> ORGANISM: Artificial
<220> FEATURE:
<223> OTHER INFORMATION: Histidine tag, including spacer

<400> SEQUENCE: 33

```
Val Asp Glu His His His His His His His His His His
1               5                   10
```

<210> SEQ ID NO 34
<211> LENGTH: 298
<212> TYPE: PRT
<213> ORGANISM: Artificial
<220> FEATURE:
<223> OTHER INFORMATION: CD16-huCAM Clone 33 bi-specific compound

<400> SEQUENCE: 34

```
Lys Trp Val Thr Phe Ile Ser Leu Leu Phe Leu Phe Ser Ser Ala Tyr
1               5                   10                  15

Ser Gln Val Gln Leu Val Glu Ser Gly Gly Gly Leu Val Gln Pro Gly
            20                  25                  30

Gly Ser Leu Arg Leu Ser Cys Ala Ala Ser Gly Leu Thr Phe Ser Ser
        35                  40                  45

Tyr Asn Met Gly Trp Phe Arg Gln Ala Pro Gly Gln Gly Leu Glu Ala
    50                  55                  60

Val Ala Ser Ile Thr Trp Ser Gly Arg Asp Thr Phe Tyr Ala Asp Ser
65                  70                  75                  80

Val Lys Gly Arg Phe Thr Ile Ser Arg Asp Asn Ser Lys Asn Thr Leu
                85                  90                  95

Tyr Leu Gln Met Asn Ser Leu Arg Ala Glu Asp Thr Ala Val Tyr Tyr
            100                 105                 110

Cys Ala Ala Asn Pro Trp Pro Val Ala Ala Pro Arg Ser Gly Thr Tyr
        115                 120                 125

Trp Gly Gln Gly Thr Leu Val Thr Val Ser Ser Ser Gly Gly Gly Gly
    130                 135                 140
```

Ser Gly Gly Gly Gly Ser Gly Gly Gly Gly Ser Gly Gly Gly Gly Ser
145 150 155 160

Gly Gly Ser Gln Val Gln Leu Leu Glu Ser Gly Gly Gly Leu Val Gln
165 170 175

Pro Gly Gly Ser Leu Arg Leu Ser Cys Ala Ala Ser Gly Asp Met Phe
180 185 190

Ser Tyr Asp Asp Met Gly Trp Val Arg Gln Ala Pro Gly Lys Gly Leu
195 200 205

Glu Trp Val Ser Gly Ile Gln Asn Thr Asp Gly Ser Thr Tyr Tyr Ala
210 215 220

Asp Ser Val Lys Gly Arg Phe Thr Ile Ser Arg Asp Asn Ser Lys Asn
225 230 235 240

Thr Leu Tyr Leu Gln Met Asn Ser Leu Arg Ala Glu Asp Thr Ala Val
245 250 255

Tyr Tyr Cys Ala Thr Leu Tyr Asp Arg Met Val Gly Lys Glu Glu Gln
260 265 270

Leu Ala Ser Trp Gly Gln Gly Thr Leu Val Thr Val Ser Ser Gly Ser
275 280 285

His His His His His His His His His His
290 295

<210> SEQ ID NO 35
<211> LENGTH: 430
<212> TYPE: PRT
<213> ORGANISM: Artificial
<220> FEATURE:
<223> OTHER INFORMATION: CD16-huCAM Clone 33 tri-specific compound

<400> SEQUENCE: 35

Lys Trp Val Thr Phe Ile Ser Leu Leu Phe Leu Phe Ser Ser Ala Tyr
1 5 10 15

Ser Gln Val Gln Leu Val Glu Ser Gly Gly Gly Leu Val Gln Pro Gly
20 25 30

Gly Ser Leu Arg Leu Ser Cys Ala Ala Ser Gly Leu Thr Phe Ser Ser
35 40 45

Tyr Asn Met Gly Trp Phe Arg Gln Ala Pro Gly Gln Gly Leu Glu Ala
50 55 60

Val Ala Ser Ile Thr Trp Ser Gly Arg Asp Thr Phe Tyr Ala Asp Ser
65 70 75 80

Val Lys Gly Arg Phe Thr Ile Ser Arg Asp Asn Ser Lys Asn Thr Leu
85 90 95

Tyr Leu Gln Met Asn Ser Leu Arg Ala Glu Asp Thr Ala Val Tyr Tyr
100 105 110

Cys Ala Ala Asn Pro Trp Pro Val Ala Ala Pro Arg Ser Gly Thr Tyr
115 120 125

Trp Gly Gln Gly Thr Leu Val Thr Val Ser Ser Ser Gly Gly Gly Gly
130 135 140

Ser Gly Gly Gly Gly Ser Gly Gly Gly Gly Ser Gly Gly Gly Gly Ser
145 150 155 160

Gly Asn Trp Val Asn Val Ile Ser Asp Leu Lys Lys Ile Glu Asp Leu
165 170 175

Ile Gln Ser Met His Ile Asp Ala Thr Leu Tyr Thr Glu Ser Asp Val
180 185 190

His Pro Ser Cys Lys Val Thr Ala Met Lys Cys Phe Leu Leu Glu Leu
195 200 205

Gln Val Ile Ser Leu Glu Ser Gly Asp Ala Ser Ile His Asp Thr Val
210 215 220

Glu Asn Leu Ile Ile Leu Ala Asn Asn Ser Leu Ser Ser Asn Gly Asn
225 230 235 240

Val Thr Glu Ser Gly Cys Lys Glu Cys Glu Glu Leu Glu Glu Lys Asn
245 250 255

Ile Lys Glu Phe Leu Gln Ser Phe Val His Ile Val Gln Met Phe Ile
260 265 270

Asn Thr Ser Gly Ser Thr Ser Gly Ser Gly Lys Pro Gly Ser Gly Glu
275 280 285

Gly Ser Thr Lys Gly Gly Ser Gln Val Gln Leu Leu Glu Ser Gly Gly
290 295 300

Gly Leu Val Gln Pro Gly Gly Ser Leu Arg Leu Ser Cys Ala Ala Ser
305 310 315 320

Gly Asp Met Phe Ser Tyr Asp Asp Met Gly Trp Val Arg Gln Ala Pro
325 330 335

Gly Lys Gly Leu Glu Trp Val Ser Gly Ile Gln Asn Thr Asp Gly Ser
340 345 350

Thr Tyr Tyr Ala Asp Ser Val Lys Gly Arg Phe Thr Ile Ser Arg Asp
355 360 365

Asn Ser Lys Asn Thr Leu Tyr Leu Gln Met Asn Ser Leu Arg Ala Glu
370 375 380

Asp Thr Ala Val Tyr Tyr Cys Ala Thr Leu Tyr Asp Arg Met Val Gly
385 390 395 400

Lys Glu Glu Gln Leu Ala Ser Trp Gly Gln Gly Thr Leu Val Thr Val
405 410 415

Ser Ser Gly Ser His His His His His His His His His His
420 425 430

<210> SEQ ID NO 36
<211> LENGTH: 18
<212> TYPE: PRT
<213> ORGANISM: Artificial
<220> FEATURE:
<223> OTHER INFORMATION: Linker

<400> SEQUENCE: 36

Gly Ser Thr Ser Gly Ser Gly Lys Pro Gly Ser Gly Glu Gly Ser Thr
1 5 10 15

Lys Gly

CLEC12A ANTIBODY FRAGMENT SEQUENCES AND METHODS

CROSS-REFERENCE TO RELATED APPLICATION

This application is the § 371 U.S. National Stage of International Application No. PCT/US2020/055468, filed Oct. 14, 2020, which claims the benefit of U.S. Provisional Patent Application No. 62/916,340, filed Oct. 17, 2019, each of which is incorporated herein by reference in its entirety.

SEQUENCE LISTING

This application contains a Sequence Listing electronically submitted to the United States Patent and Trademark Office via EFS-Web as an ASCII text file entitled "0110-000633WO01_ST25.txt" having a size of 39 KB and created on Oct. 14, 2020. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, an anti-CLEC12A polypeptide. The anti-CLEC12A polypeptide has an amino acid sequence having at least 90% amino acid similarity to SEQ ID NO:14.

In some embodiments, the anti-CLEC12A polypeptide includes the amino acid sequence of SEQ ID NO:1, the amino acid sequence of SEQ ID NO:2, the amino acid sequence of SEQ ID NO:3, the amino acid sequence of SEQ ID NO:4, the amino acid sequence of SEQ ID NO:5, the amino acid sequence of SEQ ID NO:6, the amino acid sequence of SEQ ID NO:7, the amino acid sequence of SEQ ID NO:8, the amino acid sequence of SEQ ID NO:9, the amino acid sequence of SEQ ID NO:10, the amino acid sequence of SEQ ID NO:11, the amino acid sequence of SEQ ID NO:12, or the amino acid sequence of SEQ ID NO:13.

In some embodiments, the anti-CLEC12A polypeptide includes the amino acid sequence of SEQ ID NO:29, the amino acid sequence of SEQ ID NO:30, and the amino acid sequence of SEQ ID NO:31.

In some embodiments, anti-CLEC12A polypeptide may be incorporated into an anti-CLEC12A biologic. In some of these embodiments, the anti-CLEC12A biologic can be a bi-specific Killer engager molecule (BiKE), a tri-specific Killer engager molecule (TriKE), a tetra-specific Killer engager molecule (TetraKE), a penta-specific Killer engager molecule (PentaKE), a bi-specific T cell engager molecule (BiTE), a tri-specific T cell engager molecule (TriTE), tetra-specific T cell engager molecule (TetraTE), a penta-specific T cell engager molecule (PentaTE), a chimeric antigen receptor, a full antibody, an antibody-drug conjugate (ADC) molecule, a targeted delivery construct, or a labeling construct.

In some embodiments, the anti-CLEC12A biologic may be combined with a pharmaceutically acceptable carrier to form a pharmaceutical composition.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Amino acid sequence alignment of 13 unique anti-CLEC12A antibody variant clones (SEQ ID NOS:1-13), identified by phage display, and the anti-CLEC12A antibody consensus sequence (SEQ ID NO:14). CDR1, CDR2, and CDR3 sequences are underlined.

FIG. 8. Evaluation of binding specificity of Clone 33. (A) Binding of Clone 33-containing bi-specific compound (SEQ ID NO:34) and tri-specific compound (SEQ ID NO:15) containing anti-CLEC12A scFv to CLEC12A$^{+}$HL60 cells. (B) Binding of Clone 33-containing bi-specific compound (SEQ ID NO:34) and tri-specific compound (SEQ ID NO:15) containing anti-CLEC12A scFv to CLEC12A-negative Raji cells.

DETAILED DESCRIPTION OF ILLUSTRATIVE EMBODIMENTS

C-type lectin domain family 12 member A (CLEC12A) is a protein that in humans is encoded by the CLEC12A gene. CLEC12A a member of the C-type lectin/C-type lectin-like domain (CTL/CTLD) superfamily. CLEC12A is an inhibitory C-type lectin-like receptor. It contains an immunoreceptor tyrosine-based inhibitory motif (HIM) in its cytoplasmic tail that can associate with signaling phosphatases such as, for example, SHP-1 and SHP-2.

Human CLEC12A is a monomer expressed primarily on myeloid cells such as, for example, granulocytes, monocytes, macrophages, and dendritic cells. CLEC12A is a target for immunotherapy for treating myeloid malignancies such as, for example, acute myeloid leukemia. (AML) or a myelodysplastic syndrome (MDS) since CLEC12A is expressed on the majority of myeloid blasts and leukemic stem cells (LSCS) myeloid cells but is not expressed on cells of normal tissue or normal hematopoietic stem cells.

Figure 2:
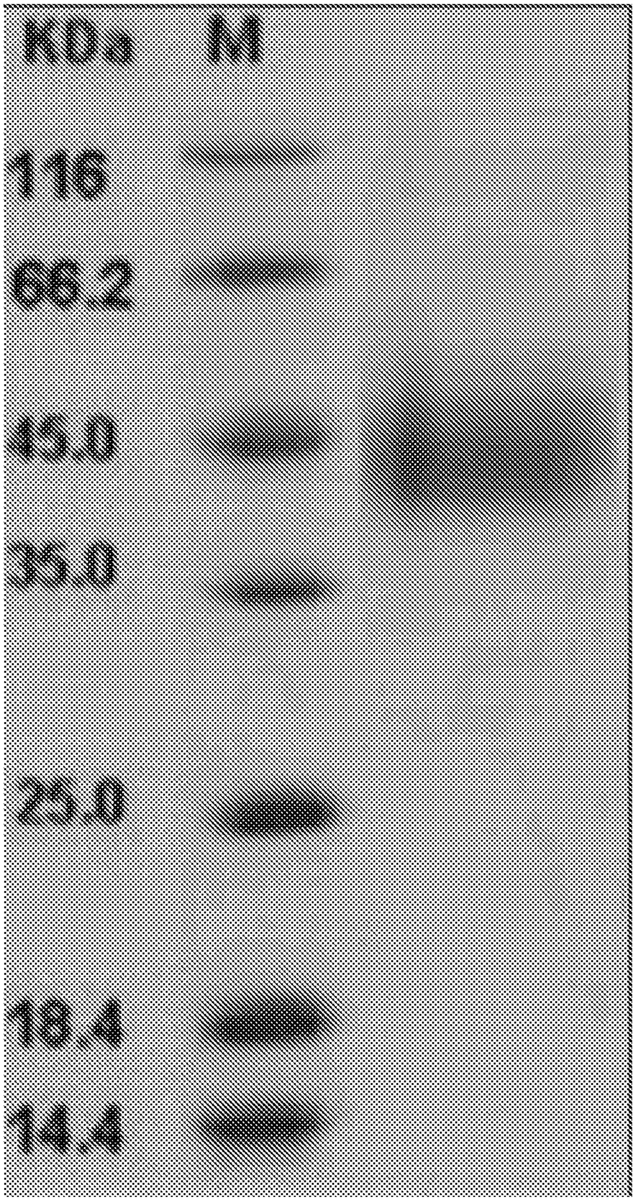
FIG. 2. SDS-PAGE of His-tagged human CLEC12A extracellular domain used for screening.

Human CLEC12 was subjected to phage display single domain antibody (sdAb) library screening. Three rounds of library panning were performed using a premade single domain antibody library for human CLEC12A. As shown in FIG. 2, the SDS-PAGE result indicated that the recombinant human CLEC12A protein was of high quality. Biopanning was then performed to enrich the specific binders to the target human CLEC12A. As shown in Table 1, after three rounds of library screening, strong enriching effect was observed for human CLEC12A, and clear difference was found between the target screening groups and no coating control groups.

TABLE 1

| Round | Input | Output | Enriching factor |
|---|---|---|---|
| 1 | $2.00 \times 10^{11}$ | $5.84 \times 10^{4}$ | $3.42 \times 10^{6}$ |
| 2 - P | $2.44 \times 10^{11}$ | $2.13 \times 10^{5}$ | $1.15 \times 10^{6}$ |
| 2 - N | $3.05 \times 10^{10}$ | $2.02 \times 10^{3}$ | $1.51 \times 10^{7}$ |
| 3 - P | $2.54 \times 10^{11}$ | $4.51 \times 10^{7}$ | $5.63 \times 10^{3}$ |
| 3 - N | $3.18 \times 10^{10}$ | $2.40 \times 10^{3}$ | $1.33 \times 10^{7}$ |

Ninety-six clones were selected from the 3rd-P eluate and subjected to monoclonal phage ELISA. Eighty-two positive clones were identified and subjected to DNA sequencing. Seventy-seven clones were sequenced successfully, and 13 unique sequences were found (SEQ ID NOS:1-13). The 13 unique sequences were aligned, yielding a consensus sequence (SEQ ID NO:14) and identifying complementarity-determining regions (CDRs), as shown in FIG. 1.

After sequencing, the 13 unique sequences were cloned into the soluble VHH-AP expression vector and subjected to soluble expression and soluble ELISA. As shown in Table 2, all 13 clones bound to human CLEC12A positively.

TABLE 2

| Monoclonal phage ELISA | | | |
|---|---|---|---|
| Clone | Induce Temp | CLEC12A | No Coating |
| 1 | 30° C. | 0.1900 | 0.1740 |
| | 37° C. | 2.0060 | 0.3150 |
| 3 | 30° C. | 0.2240 | 0.1570 |
| | 37° C. | 0.3640 | 0.1870 |
| 9 | 30° C. | 0.3910 | 0.1700 |
| | 37° C. | 0.4720 | 0.2080 |
| 10 | 30° C. | 0.3480 | 0.1830 |
| | 37° C. | 0.6020 | 0.3280 |
| 11 | 30° C. | 1.4340 | 0.3250 |
| | 37° C. | 1.4510 | 0.3650 |
| 17 | 30° C. | 0.9840 | 0.2300 |
| | 37° C. | 0.6100 | 0.2370 |
| 23 | 30° C. | 0.6690 | 0.1590 |
| | 37° C. | 0.7120 | 0.1640 |
| 29 | 30° C. | 1.2190 | 0.2290 |
| | 37° C. | 1.3380 | 0.1750 |
| 33 | 30° C. | 1.5930 | 0.1820 |
| | 37° C. | 1.5190 | 0.1990 |
| 40 | 30° C. | 09.190 | 0.2110 |
| | 37° C. | 0.9040 | 0.3040 |
| 56 | 30° C. | 0.2920 | 0.1860 |
| | 37° C. | 0.4370 | 0.2760 |
| 60 | 30° C. | 0.7130 | 0.2140 |
| | 37° C. | 0.6900 | 0.2920 |
| 86 | 30° C. | 1.6750 | 0.1620 |
| | 37° C. | 1.7080 | 0.1610 |
| TG1 Lysate | — | 0.1430 | 0.1670 |
| TBS | — | 0.1560 | 0.1660 |

Figure 3:
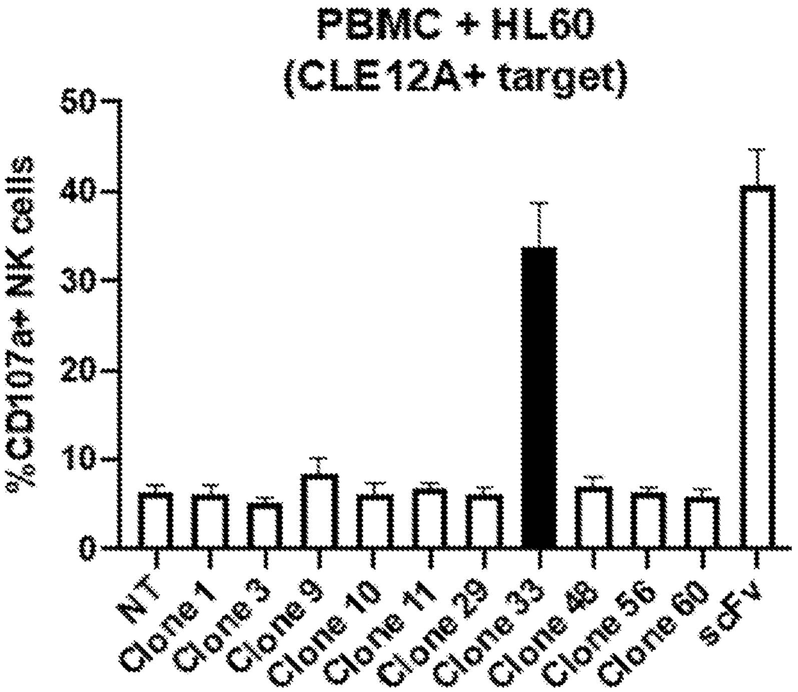
FIG. 3. Functional screening of bi-specific compounds containing humanized camelid (huCAM) anti-CLEC12A antibody fragments using PBMCs. Peripheral blood mononuclear cells (PBMCs) were incubated with the CLEC12A-expressing promyelocytic leukemia cell line HL60 in the presence of noted bi-specific compounds containing the different clones (SEQ ID NOs:1-13). A tri-specific compound (SEQ ID NO:15) containing an anti-CLEC12A scFv and known to target CLEC12A was used a positive control, while no treatment (NT) was used as a negative control. After five hours in culture, cells were harvested, stained for surface antigens, fixed, permeabilized, and stained for intracellular interferon gamma (IFNγ). Cells were run on a flow cytometer and NK cell activation was measured via evaluation of degranulation (CD107a) of $CD56^{+}CD3^{-}$ NK cells.
Figure 4:
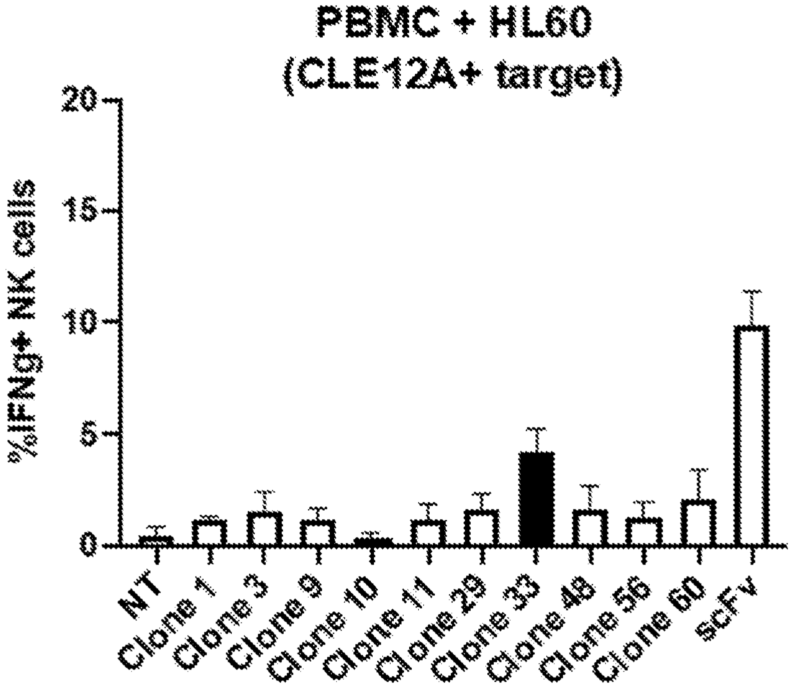
FIG. 4. Functional screening of bi-specific compounds containing humanized camelid (huCAM) anti-CLEC12A antibody fragments using PBMCs. Peripheral blood mononuclear cells (PBMCs) were incubated with the CLEC12A-expressing promyelocytic leukemia cell line HL60 in the presence of noted bi-specific compounds containing the different clones (SEQ ID NOs:1-13). A tri-specific compound (SEQ ID NO:15) containing an anti-CLEC12A scFv and known to target CLEC12A was used a positive control, while no treatment (NT) was used as a negative control. After five hours in culture, cells were harvested, stained for surface antigens, fixed, permeabilized, and stained for intracellular interferon gamma (IFNγ). Cells were run on a flow cytometer and NK cell activation was measured via evaluation of IFNγ production by $CD56^{+}CD3^{-}$ NK cells.

FIG. 3 and FIG. 4 show the functional screening of humanized camelid (huCAM) anti-CLEC12A clones using PBMCs. The humanized anti-CLEC12A camelid clone variants (SEQ ID NOs:1-13) were cloned as the targeting domain into a bi-specific backbone containing a camelid anti-CD16 and a linker. These bi-specific compounds activated natural killer (NK) cells through formation of a cytolytic bridge between the NK cell (through binding of CD16) and the tumor cell through binding of CLEC12A. A tri-specific killer engager (SEQ ID NO:15) previously tested and shown to target CLEC12A through a single chain variable fragment (scFv) was used as a positive control. The data show that Clone 33 displays the highest activity. Some clones were produced in smaller amounts and thus were tested at lower concentrations than the scFv (tri-specific positive control) or the Clone 33 bi-specific compound.

Thus, no conclusions can be drawn from results where a clone appears to lack activity compared to the negative control.

Figure 5:
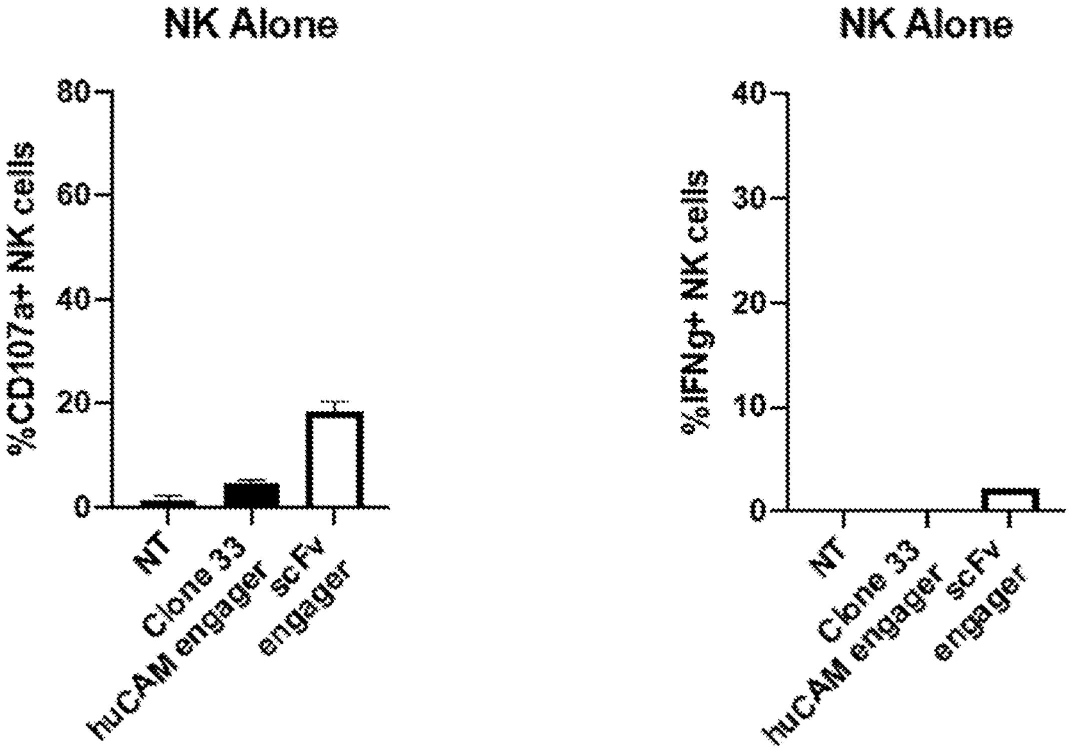
FIG. 5. Evaluation of a bi-specific compound containing humanized camelid (huCAM) anti-CLEC12A Clone 33. To determine background activation mediated by the Clone 33 bi-specific compound, enriched NK cells were incubated with the bi-specific compound containing anti-CLEC12A Clone 33 (Clone 33 huCAM engager), the CLEC12A tri-specific compound (SEQ ID NO:15; scFv engager), or no compound (NT) for five hours. NK cell degranulation (CD107a, left) and cytokine production (IFNγ, right) were measured by flow cytometry. While the scFv shows some background activation in terms of degranulation, Clone 33 doesn't, highlighting better specificity.
Figure 6:
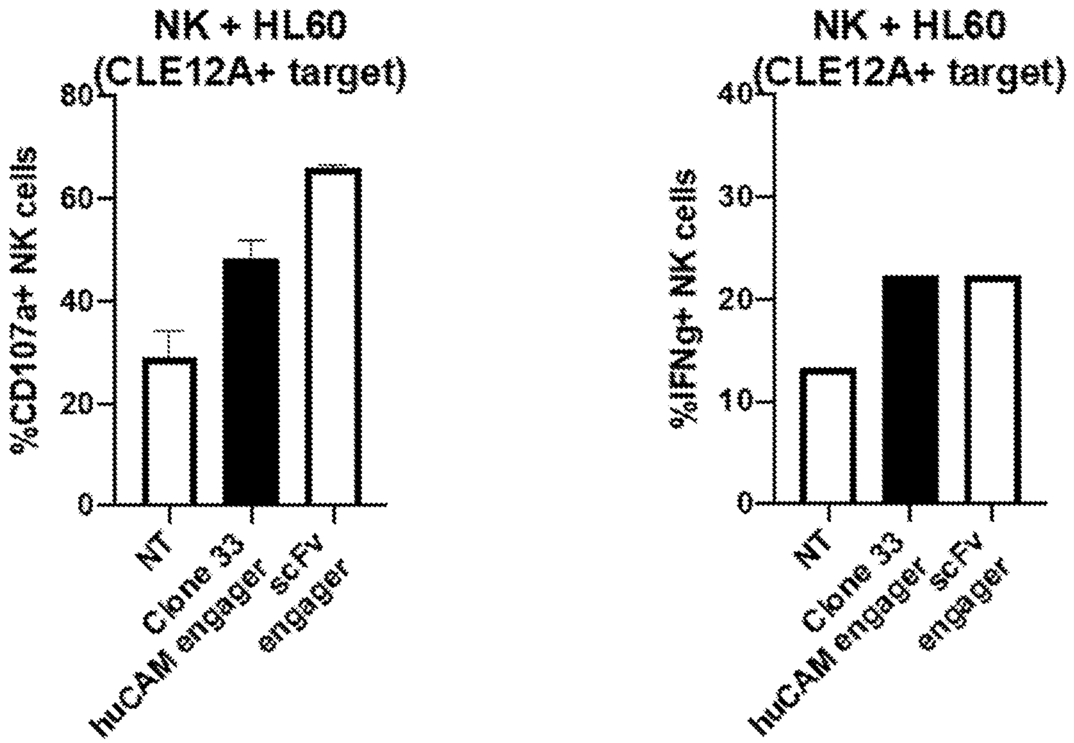
FIG. 6. Evaluation of a bi-specific compound containing humanized camelid (huCAM) anti-CLEC12A Clone 33. To determine activation mediated by the bi-specific compound containing the anti-CLEC12A Clone 33 against a CLEC12-expressing target, enriched NK cells were incubated with HL60 cells and either the bi-specific compound (SEQ ID NO:34) containing anti-CLEC12A Clone 33 (Clone 33 huCAM engager), the CLEC12A tri-specific compound (SEQ ID NO:15; scFv engager), or no compound (NT) for five hours. NK cell degranulation (CD107a, left) and cytokine production (IFNγ, right) were measured by flow cytometry. The Clone 33-containing tri-specific compound induces NK cell degranulation against HL60 targets and induces the same amount of cytokine production as the scFv-containing positive control.
Figure 7:
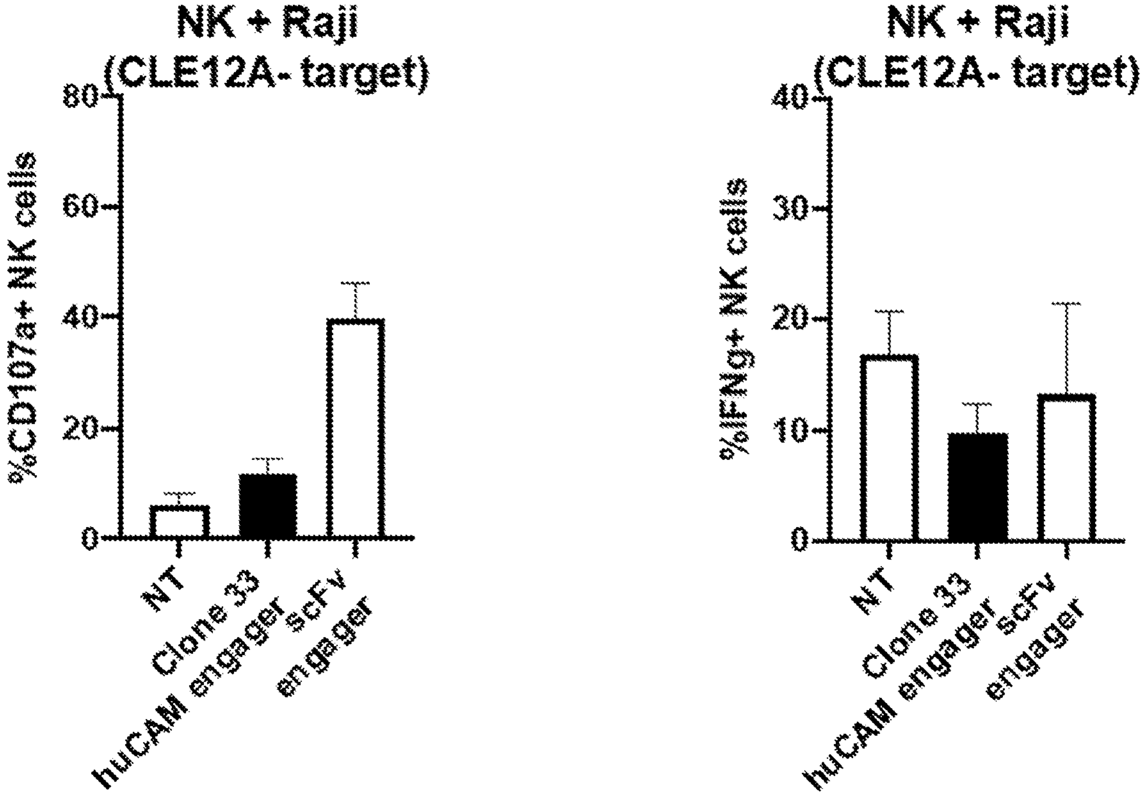
FIG. 7. Evaluation of a bi-specific compound containing humanized camelid (huCAM) anti-CLEC12A Clone 33. To determine activation mediated by the bi-specific compound containing the anti-CLEC12A Clone 33 against a CLEC12-negative target (non-specific activation), enriched NK cells were incubated with Raji (Burkitt's lymphoma) cells and either the bi-specific compound (SEQ ID NO:34) containing anti-CLEC12A Clone 33 (Clone 33 huCAM engager), the CLEC12A tri-specific compound (SEQ ID NO:15; scFv engager), or no compound (NT) for five hours. NK cell degranulation (CD107a, left) and cytokine production (IFNγ, right) were measured by flow cytometry. The Clone 33-containing bi-specific compound induces less non-specific degranulation against CLEC12A-negative targets than the tri-specific compound containing the anti-CLEC12A scFv.

To determine the functional specificity of the humanized CLEC12A camelid Clone 33 antibody fragment, the CD16-Clone 33 bi-specific compound (SEQ ID NO:34) was used. This bi-specific compound has the ability to activate natural killer (NK) cells through formation of a cytolytic bridge between an NK cell (through binding of CD16) and a tumor cell (through binding of CLEC12A). FIG. 5. shows background activation of NK cells as measured by NK cell degranulation (CD107a, left) and induction of IFNγ (right). The bi-specific compound containing Clone 33 shows minimal background NK cell activation. FIG. 6 shows activation of NK cells in the presence of CLEC12A-positive HL60 cells. The bi-specific compound containing the anti-CLEC12A Clone 33 antibody fragment induced both degranulation (left) and production of IFNγ (right), with IFNγ induction being nearly identical to the positive control, the anti-CLEC12A-scFv-containing tri-specific compound (SEQ ID NO:15). FIG. 7. shows NK activation in the presence of CLEC12A-negative Raji (Burkitt's lymphoma) cells. The Clone-33-containing bi-specific compound induces less non-specific degranulation against a CLEC12A-negative target than the anti-CLEC12A-scFv-containing tri-specific compound.

FIG. 8 further shows the binding specificity of the anti-CLEC12A Clone 33. Both the bi-specific compound containing the anti-CLEC12A Clone 33 antibody fragment and the tri-specific compound containing the anti-CLEC12A scFv were constructed in include a 10×HIS tag. Binding of these constructs to CLEC12A-positive HL60 cells (FIG. 8A) and CLEC12A-negative Raji cells (FIG. 8B) was assessed using an anti-HIS-Phycoerythrin-labeled antibody. As a control, basal binding of the anti-HIS-PE antibody was determined without previous binding of the engager compounds (gray bars). As the data shows, both the Clone 33 bi-specific compound and the scFv tri-specific compound induced minimal binding against CLEC12A negative cells. The Clone 33 bi-specific compound induced more binding to the CLEC12A-positive cells than the anti-CLEC12A scFv-containing tri-specific compound.

Thus, this disclosure describes polypeptides that target CLEC12A on myeloid malignancies. Because the polypeptides target CLEC12A, the polypeptides induce less targeting of normal myeloid cells than polypeptides that target other antigens associated with myeloid malignancies such as, for example, CD33. This disclosure expressly describes 12 unique humanized single-domain antibody (sdAb) sequences that target CLEC12A, a consensus sequence derived from an alignment of the 12 unique anti-CLEC12A sdAb sequences, and provides guidance toward additional variants by identifying regions of high conservation and regions of variability among the 13 total sequences.

The anti-CLEC12A polypeptides described herein can be incorporated into biologic constructs that may be used in the context of, for example, therapeutic, diagnostic, and/or detection methods. For example, the anti-CLEC12A polypeptides described herein may be incorporated into a bi-specific Killer engager molecule (BiKE, e.g., SEQ ID NO:34), a tri-specific Killer engager molecule (TriKE, e.g., SEQ ID NO:35), a tetra-specific Killer engager molecule (TetraKE), a penta-specific Killer engager molecule (PentaKE), a bi-specific T cell engager molecule (BiTE), a tri-specific T cell engager molecule (TriTE), a tetra-specific T cell engager molecule (TetraTE), a penta-specific T cell engager molecule (PentaTE), a chimeric antigen receptor (CAR, for expression in, for example, CAR T cells, CAR NK cells, CAR macrophage cells, etc.), a full antibody construct (e.g., to induce antibody-dependent cellular toxicity (ADCC)), an antibody-drug conjugate (ADC) molecule (e.g., for delivery of a toxin), a labeling construct (e.g., for commercial evaluation of antigen expression), a radiolabeled format (e.g., for positron-emission tomography (PET) imaging or directed radiation delivery), an applications for delivery of a cytokine and/or a chemokine, or other general immunotherapeutic approach.

While other reagents—e.g., CD33-binding antibodies and/or antibody fragments—target myeloid malignancies expressing CD33, they also target normal myeloid cells that express lower levels of the target. In contrast, the anti-CLEC12A polypeptides described herein are much less likely to result in on-target, off-tumor toxicity by targeting an antigen that is more specifically expressed on myeloid malignancies (e.g., such as acute myeloid leukemia (AML) cells or myelodysplastic syndromes (MDS) cells). CLEC12A is also expressed in leukemic stem cells. Thus, targeting CLEC12A can limit the likelihood and/or severity of relapse. The anti-CLEC12A polypeptides described herein also may provide advantages over scFvs for forming constructs (e.g., BiKEs, TriKEs, BiTEs, CARs, etc) because sdAbs are more stable than scFvs. Finally, the anti-CLEC12A sequences described herein are all from a humanized library, and thus less likely to rejected in human patients.

This disclosure describes anti-CLEC12A polypeptides. Exemplary anti-CLEC12A polypeptides include polypeptides that include, or are structurally similar to, or are functional variants of, the amino acid sequence of any one of SEQ ID NOs:1-14 or SEQ ID NOs:29-31. SEQ ID NOs:1-13 are variant single domain antibody sequences selected through phage display screening because they specifically bind to CLEC12A. SEQ ID NO:14 is a consensus sequence derived from an alignment analysis of SEQ ID NOs:1-13 (FIG. 1). SEQ ID NO:29 is the consensus sequence of CDR1 as determined from the alignment analysis shown in FIG. 1. SEQ ID NO:30 is the consensus sequence of CDR2 as determined from the alignment analysis shown in FIG. 1. SEQ ID NO:31 is the consensus sequence of CDR3 as determined from the alignment analysis shown in FIG. 1.

As used herein, an anti-CLEC12A polypeptide is "structurally similar" to or a "functional variant" of a reference polypeptide if the amino acid sequence of the anti-CLEC12A polypeptide possesses a specified amount of identity compared to the reference polypeptide. An amino acid sequence is a "functional fragment" of a reference amino acid sequence if the "functional fragment" amino acid sequence contains less than the full-length amino acid sequence of the reference amino acid sequence. A "functional fragment" may further possess a specified amount of sequence identity or sequence specificity compared to the reference amino acid sequence.

Structural similarity and/or sequence identity of two polypeptides can be determined by aligning the amino acid residues of the two polypeptides (for example, a candidate anti-CLEC12A polypeptide and the polypeptide of, for example, any one of SEQ ID NOs:1-14 or SEQ ID NOs: 29-31) to optimize the number of identical amino acids along the lengths of their sequences. Gaps in either or both sequences are permitted in making the alignment in order to optimize the number of identical amino acids, although the amino acids in each sequence must nonetheless remain in their proper order. A candidate anti-CLEC12A polypeptide is the polypeptide being compared to the reference polypeptide (e.g., any one of SEQ ID NOs:1-14 or SEQ ID NOs: 29-31). A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison WI). Alternatively, polypeptides may be compared using the Blastp program of the BLAST 2 search algorithm, as described by Tatusova et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in an anti-CLEC12A polypeptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —$NH_2$. Likewise, biologically active analogs of a polypeptide containing deletions or additions of one or more contiguous or noncontiguous amino acids that do not eliminate a functional activity of the polypeptide are also contemplated.

In some embodiments, an anti-CLEC12A polypeptide as described herein can include a polypeptide with at least 90%, at least 91%, at least 92%, at least 93%, at least 94%, at least 95%, at least 96%, at least 97%, at least 98%, or at least 99% amino acid sequence similarity to the reference amino acid sequence.

In some embodiments, an anti-CLEC12A polypeptide as described herein can include at least 90%, at least 91%, at least 92%, at least 93%, at least 94%, at least 95%, at least 96%, at least 97%, at least 98%, or at least 99% amino acid sequence identity to the reference amino acid sequence.

In some embodiments, an anti-CLEC12A polypeptide as described herein also can be designed to provide additional sequences, such as, for example, amino acids added C-terminal or N-terminal of the anti-CLEC12A polypeptide. Such additional amino acids may include, for example, a signal sequence (e.g., SEQ ID NO:32) or a tag that facilitates purification by trapping the tagged anti-CLEC12A polypeptide on a column or by using antibodies. Exemplary tags include, for example, a histidine-rich tag (e.g., SEQ ID NO:33) that allows purification of polypeptides on nickel columns.

This disclosure also describes polynucleotides that encode an anti-CLEC12A polypeptide. Exemplary polynucleotides that encode an anti-CLEC12A polypeptide include the polynucleotides that include the nucleotide sequence of any one of SEQ ID NOs:16-28. SEQ ID NOs:16-28 are, however, merely exemplary. Since the genetic code is well-known, this disclosure describes any polynucleotide that encodes an anti-CLEC12A polypeptide as described herein.

An anti-CLEC12A polypeptide as described herein may be incorporated into a biologic, which is then formulated with a pharmaceutically acceptable carrier. As used herein, an "anti-CLEC12A biologic" is a biologic compound that includes an anti-CLEC12A polypeptide. An anti-CLEC12A biologic may include additional functional moieties depending on the fundamental structural platform of the biologic (e.g., a BiKE, a TriKE, a CAR, etc.). As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the anti-CLEC12A biologic without causing any undesirable biological effects or interacting in a deleterious manner with any of the other components of the pharmaceutical composition in which it is contained.

An anti-CLEC12A biologic may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, an anti-CLEC12A biologic may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the anti-CLEC12A biologic into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

Thus, in another aspect, this disclosure describes a method of treating any condition where targeting cells that overexpress CLEC12A has therapeutic benefit. In many embodiments, the condition can be a myeloid malignancy. In other embodiments, however, the condition may be an autoimmune condition—e.g., a condition in which myeloid cells infiltrate the central nervous system. Generally, the method includes administering to the subject an amount of the anti-CLEC12A biologic effective for treating the condition. "Treat" or variations thereof refer to reducing, limiting progression, ameliorating, or resolving, to any extent, the symptoms or signs related to a condition. As used herein, "ameliorate" refers to any reduction in the extent, severity, frequency, and/or likelihood of a symptom or clinical sign characteristic of a particular condition; "symptom" refers to any subjective evidence of disease or of a patient's condition; and "sign" or "clinical sign" refers to an objective physical finding relating to a particular condition capable of being found by one other than the patient.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Thus, in certain embodiments, the method can involve prophylactic treatment of a subject at risk of developing a condition. "At risk" refers to a subject that may or may not actually possess the described risk. Thus, for example, a subject "at risk" for developing a specified condition is a subject that possesses one or more indicia of increased risk of having, or developing, the specified condition compared to individuals who lack the one or more indicia, regardless of the whether the subject manifests any symptom or clinical sign of having or developing the condition. Exemplary indicia of a condition can include, for example, genetic predisposition, ancestry, age, sex, geographical location, lifestyle, or medical history. Treatment may also be continued after symptoms have resolved, for example to prevent or delay their recurrence.

In some embodiments, "prophylactic" treatment also includes treatment in the setting of relapse. In other words, a subject may have once manifested symptoms or clinical signs of a condition, but received successful treatment so that the condition is considered to be in remission. Such as subject may no longer manifest a symptom or clinical sign of the condition in remission, but be "at risk" of relapse. In such a context, treatment that includes the anti-CLEC12A biologic may be considered "prophylactic" to reduce the likelihood and/or severity of relapse.

Accordingly, an anti-CLEC12A biologic may be administered to the subject before, during, or after the subject first exhibits a symptom or clinical sign of the condition. Treatment initiated before the subject first exhibits a symptom or clinical sign associated with the condition may result in decreasing the likelihood that the subject experiences clinical evidence of the condition compared to a subject to which the anti-CLEC12A biologic is not administered, decreasing the severity of symptoms and/or clinical signs of the condition, and/or completely resolving the condition. Treatment initiated before the subject first exhibits a symptom or clinical sign associated with relapse of the condition may result in decreasing the likelihood that the subject experiences clinical evidence of relapse compared to a subject to which the anti-CLEC12A biologic is not administered, decreasing the severity of symptoms and/or clinical signs of relapse, and/or completely resolving the condition. Treatment initiated while the subject exhibits a symptom or clinical sign associated with the condition may result in decreasing the severity of symptoms and/or clinical signs of the condition compared to a subject to which the anti-CLEC12A biologic is not administered, and/or completely resolving the condition.

The amount of an anti-CLEC12A biologic administered can vary depending on various factors including, but not limited to, the specific anti-CLEC12A biologic being administered, the weight, physical condition, and/or age of the subject, and/or the route of administration. Thus, the absolute weight of anti-CLEC12A biologic included in a given unit dosage form can vary widely, and depends upon factors such as the species, age, weight and physical condition of the subject, and/or the method of administration. Accordingly, it is not practical to set forth generally the amount that constitutes an amount of anti-CLEC12A biologic effective for all possible applications. Those of ordinary skill in the art, however, can readily determine the appropriate amount with due consideration of such factors.

In some embodiments, the method can include administering sufficient anti-CLEC12A biologic to provide a dose of, for example, from about 100 ng/kg/day to about 50 mg/kg/day to the subject, although in some embodiments the methods may be performed by administering anti-CLEC12A biologic in a dose outside this range.

In some embodiments, the method can includes administering sufficient anti-CLEC12A biologic to provide a minimum dose of at least 100 ng/kg/day such as, for example, at least 1 μg/kg/day, at least 5 μg/kg/day, at least 10 μg/kg/day, at least 25 μg/kg/day, at least 50 μg/kg/day, at least 100 μg/kg/day, at least 200 μg/kg/day, at least 300 μg/kg/day, at least 400 μg/kg/day, at least 500 μg/kg/day, at least 600 μg/kg/day, at least 700 μg/kg/day, at least 800 μg/kg/day, at least 900 μg/kg/day, or at least 1 mg/kg/day.

In some embodiments, the method includes administering sufficient anti-CLEC12A biologic to provide a maximum dose of no more than 10 mg/kg/day such as, for example, no more than 5 mg/kg/day, no more than 4 mg/kg/day, no more than 3 mg/kg/day, no more than 2 mg/kg/day, no more than 1 mg/kg/day, no more than 900 μg/kg/day, no more than 800 μg/kg/day, no more than 700 μg/kg/day, no more than 600 μg/kg/day, no more than 500 μg/kg/day, no more than 400 μg/kg/day, no more than 300 μg/kg/day, no more than 200 μg/kg/day, no more than 100 μg/kg/day, no more than 90 μg/kg/day, no more than 80 μg/kg/day, no more than 70 μg/kg/day, no more than 60 μg/kg/day, no more than 50 μg/kg/day, no more than 40 μg/kg/day, no more than 30 μg/kg/day, no more than 20 μg/kg/day, or no more than 10 μg/kg/day. The anti-CLEC12A biologic provides a dose of "no greater than" a specified amount when the anti-CLEC12A biologic is not absent but is present in an amount up to and including the specified amount.

In some embodiments, the method includes administering sufficient anti-CLEC12A biologic to provide a dose characterized by a range having endpoints defined by any a minimum dose identified above and any maximum dose that is greater than the selected minimum dose. For example, in some embodiments, the method can include administering sufficient anti-CLEC12A biologic to provide a dose of from about 10 μg/kg/day to about 10 mg/kg/day to the subject, a dose of from about 100 μg/kg/day to about 1 mg/kg/day, a dose of from 5 μg/kg/day to 100 μg/kg/day, etc.

In certain embodiments, the method includes administering sufficient anti-CLEC12A biologic to provide a dose that is equal to any minimum dose or any maximum dose listed above. Thus, for example, in certain embodiments, the method can include administering sufficient anti-CLEC12A biologic to provide a dose of 1 μg/kg/day, 5 μg/kg/day, 10 μg/kg/day, 25 μg/kg/day, 50 μg/kg/day, 100 μg/kg/day, 200 μg/kg/day, 500 μg/kg/day, 1 mg/kg/day, 5 mg/kg/day, etc.

In some embodiments, an anti-CLEC12A biologic may be administered, for example, from a single dose to multiple doses per week, although in some embodiments the method can be performed by administering an anti-CLEC12A biologic at a frequency outside this range. In certain embodiments, an anti-CLEC12A biologic may be administered from about once per month to about five times per week. In some embodiments, the doses indicated above, which are described in terms of the amount of anti-CLEC12A biologic administered over a 24-hour period, are administered in a seven-day cycle of four days of treatment and three days of rest.

In some embodiments, an anti-CLEC12A biologic may be administered, for example, from a single dose to multiple cycles of treatment, although in some embodiments the method can be performed by administering an anti-CLEC12A biologic for a duration outside this range. In some embodiments, the anti-CLEC12A biologic may be administered for three weeks. In such embodiments, each week may be a treatment cycle such as the exemplary treatment cycle described in the preceding paragraph. In other embodiments, the anti-CLEC12A biologic may be administered for a greater number of treatment cycles, without a gap between one set of treatment cycles and a subsequent set of treatment cycles. The gap between one set of treatment cycles and a subsequent set of treatment cycles may be a gap of one or more weeks, one or more months, or one or more years.

In some embodiments, the method further includes administering one or more additional therapeutic agents. The one or more additional therapeutic agents (e.g., chemotherapeutic agents) may be administered before, after, and/or coincident to the administration of an anti-CLEC12A biologic. An anti-CLEC12A biologic and the additional therapeutic agents may be co-administered. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another. In other embodiments, the anti-CLEC12A biologic and the additional therapeutic agent may be administered as part of a mixture or cocktail. In some aspects, the administration of anti-CLEC12A biologic may allow for the effectiveness of a lower dosage of other therapeutic modalities when compared to the administration of the other therapeutic agent or agents alone, thereby decreasing the likelihood, severity, and/or extent of the toxicity observed when a higher dose of the other therapeutic agent or agents is administered.

Exemplary additional therapeutic agents include altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, and vinorelbine.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

EXAMPLES

Construction of the CD16-huCAMCLEC12A Bi-Specific Compound (SEQ ID NO:34)

Constructs encoding the CD16-huCAMCLEC12A bi-specific compounds were synthesized using PCR and HiFi cloning techniques as previously described (Vallera et al., 2016, *Clin Cancer Res* 22:3440-3450). Each fully assembled fragment included an EcoRI restriction site, an ATG start codon, the coding sequence for a humanized camelid anti-CD16 sdAb (Behar et al., 2008, *Protein Eng Des Sel* 21:1-10), the coding sequence for a huCAMCLEC12A sdAb (one of SEQ ID NOs:16-28), and a sequence encoding a 10×His tag. The assembled fragments were cloned into the Minicircle DNA vector (System Biosciences, LLC, Palo Alto, CA) under the control of a CMV promoter. The DNA sequence was validated to confirm sequence and location of gene insertion (Biomedical Genomics Center, University of Minnesota, Minneapolis, MN).

Construction of the CD16-huCAMCLEC12A Tri-Specific Compound (SEQ ID NO:35)

Constructs encoding the CD16-huCAMCLEC12A tri-specific compounds were synthesized using PCR and HiFi cloning techniques as previously described (Vallera et al., 2016, *Clin Cancer Res* 22:3440-3450). Each fully assembled fragment included an EcoRI restriction site, an ATG start codon, the coding sequence for a humanized camelid anti-CD16 sdAb (Behar et al., 2008, *Protein Eng Des Sel* 21:1-10), a linker, the coding sequence for a human IL-15 fragment (amino acids 162-175 of SEQ ID NO:35), the coding sequence for a whitlow amino acid linker (GSTSGSGKPGSGEGSTKG; SEQ ID NO:36), the coding sequence for a huCAMCLEC12A sdAb (one of SEQ ID NOs:16-28), and a sequence encoding a 10×His tag. The assembled fragments were cloned into the Minicircle DNA vector (System Biosciences, LLC, Palo Alto, CA) under the control of a CMV promoter. The DNA sequence was validated to confirm sequence and location of gene insertion (Biomedical Genomics Center, University of Minnesota, Minneapolis, MN).

Production and Isolation of CD16-huCAMCLEC12A Bi-Specific Compounds and CD16-huCAMCLEC12A Tri-Specific Compound Plasmids for all clones were transfected into Expi293 cells (Thermo Fisher Scientific, Inc., Waltham, MA) according to the manufacturer's protocol. The supernatants were collected, and protein was purified using HISPUR cobalt resin (Thermo Fisher Scientific, Inc., Waltham, MA) and PIERCE centrifuge columns (Thermo Fisher Scientific, Inc., Waltham, MA). The protein was eluted using 250 mM imidazole solution and desalted using prepacked disposable PD-10 columns (GE Healthcare Systems, Chicago, IL). Purity and size were determined by running sodium dodecyl sulfate polyacrylamide gel electrophoresis using SIMPLY BLUE LIFE STAIN (Invitrogen, Carlsbad, CA).

Cancer Cells Lines (HL60 and Raji)

HL60 promyeloblast cells (ATCC CCL-240, American Type Culture Collection, Manassas, VA) where obtained from ATCC and used as a CLEC12A-expressing line. Raji Burkitt's lymphoma lymphoblasts (ATCC CCL-86, American Type Culture Collection, Manassas, VA) were also obtained from ATCC and used as a CLEC12A-negative line.

Functional Evaluation of Different Clones Using PBMCs Against CLEC12A-Positive HL60 Cells Healthy donor blood was obtained from Memorial Blood Bank (Minneapolis, MN) and processed to obtain peripheral blood mononuclear cells (PBMCs) using density gradient Ficoll-Paque (GE Healthcare Systems, Chicago, IL). Assessment of NK cell function by flow cytometry was carried out as previously described (Vallera et al., 2016, *Clin Cancer Res* 22:3440-3450). PBMCs, HL60 cells, and treatments (30 nM) were co-cultured and stained with FITC conjugated anti-CD107a (H4A3, BioLegend, San Diego, CA). One hour after the addition of anti-CD107a, cells were given Golgi Stop and Golgi Plug (BD Biosciences, San Jose, CA) and incubated for three hours. At the end of the incubation, cells were stained with Live/Dead Fixable Aqua Staining Kit (Thermo Fisher Scientific, Inc., Waltham, MA), PE-CY7-conjugated anti-CD56, PE-CF594-conjugated anti-CD3, and PE-conjugated anti-CD69 (FN50, BioLegend, San Diego, CA), fixed, and permeabilized. Permeabilized cells were stained with BV650 conjugated IFNγ (4S.B3, BioLegend, San Diego, CA) and expression was evaluated by flow cytometry.

Evaluation of Functional Specificity of Clone 33 Using NK Cells Against Nothing, CLEC12A-Positive HL60 Cells, or CLEC12A-Negative Raji Cells Healthy donor blood was obtained from Memorial Blood Bank (Minneapolis, MN) and processed to obtain peripheral blood mononuclear cells (PBMCs) using density gradient FICOLL-PAQUE (GE Healthcare Systems, Chicago, IL). PBMCs were used to magnetically enrich NK cells using an EASYSEP human NK cell enrichment kit (STEMCELL Technologies, Inc., Vancouver, BC). Assessment of NK cell function by flow cytometry was carried out as previously described (Vallera et al., 2016, *Clin Cancer Res* 22:3440-3450). Enriched NK cells were incubated alone, with HL60 cells, or with Raji cells and noted treatments (30 nM). Cells and treatments were co-cultured and stained with FITC conjugated anti-CD107a (H4A3, BioLegend, San Diego, CA). One hour after the addition of anti-CD107a, cells were given Golgi Stop and Golgi Plug (BD Biosciences, San Jose, CA) and incubated for three hours. At the end of the incubation, cells were stained with Live/Dead Fixable Aqua Staining Kit (Thermo Fisher Scientific, Inc., Waltham, MA), PE-CY7-conjugated anti-CD56, PE-CF594-conjugated anti-CD3, and PE-conjugated anti-CD69 (BioLegend, San Diego, CA), fixed, and permeabilized. Permeabilized cells were stained with BV650-conjugated IFNγ (BioLegend, San Diego, CA) and expression was evaluated by flow cytometry.

Determination of Binding Specificity

To determine binding specificity, 30 nM of the Clone 33 bi-specific compound or the anti-CLEC12A scFv-containing tri-specific compound were incubated with CLEC12A-positive HL60 cells or CLEC12A-negative Raji cells for 30 minutes at 37° C. The cells were spun down and washed twice. An anti-HIS, phycoerythrin (PE)-labeled, antibody (OriGene Technologies, Inc., Rockville, MD) was added and incubated with cells for 20 minutes at 4° C. Cells were washed twice, fixed with 2% paraformaldehyde, and run on a flow cytometer to evaluate percent of cells binding to noted constructs.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

```
SEQ ID NO: 1-CLEC12A clone 1
  1       QVQLQESGGG LVQPGGSLRL SCAASGDRES NDVMAWVRQA PGKGLEWVSA
 51       IVTQDGSTYY ADSVKGRFTI SRDNSKNTLY LQMNSLRAED TAVYYCAGEP
101       LDAEDLWYWG QGTLVTVSS

SEQ ID NO: 2-CLEC12A clone 3
  1       QVQLLESGGG LVQPGGSLRL SCAASGVRVS AQFMSWVRQA PGKGLEWVSS
 51       IYKKNGSTYY ADSVKGRFTI SRDNSKNTLY LQMNSLRAED TAVYYCAIDH
101       GEEHKELYSW GQGTLVTVSS

SEQ ID NO: 3-CLEC12A clone 9
  1       QVQLLESGGG LVQPGGSLRL SCAASGYSIT DQDMSWVRQA PGKGLEWVSG
 51       ILATSGSTYY ADSVKGRFTI SRDNSKNTLY LQMNSLRAED TAVYYCAGEV
101       EKSSQSMPFW GQGTLVTVSS

SEQ ID NO: 4-CLEC12A clone 10
  1       QVQLLESGGG LVQPGGSLRL SCAASGVNVT ADDMSWVRQA PGKGLEWVST
 51       IDGGDGSTYY ADSVKGRFTI SRDNSKNTLY LQMNSLRAED TAVYYCATAF
101       TSHEAEVHSW GQGTLVTVSS

SEQ ID NO: 5-CLEC12A clone 11
  1       QVQLLESGGG LVQPGGSLRL SCAASGYRLS NDIMAWVRQA PGKGLEWVSA
 51       IVDTDGSTYY ADSVKGRFTI SRDNSKNTLY LQMNSLRAED TAVYYCARDP
101       YNEDDVSYWG QGTLVTVSS

SEQ ID NO: 6-CLEC12A clone 17
  1       QVQLLESGGG LVQPGGSLRL SCAASGERFI AQDMSWVRQA TGKGLEWVST
 51       IATNDGSTYY ADSVKGRFTI SRDNSKNTLY LQMNSLRAED TAVYYCATDS
101       SWENDLWYWG QGTLVTVSS

SEQ ID NO: 7-CLEC12A clone 23
  1       QVQLLESGGG LVQPGGSLRL SCAASGERLT DEDMSWVRQA PGKGLEWVST
 51       IATRDGSTYY ADSVKGRFTI SRDNSKNTLY LQMNSLRAED TAVYYCAGLR
101       DQLYGNEQLA FWGQGTLVTV SS

SEQ ID NO: 8-CLEC12A clone 29
  1       QVQLLESGGG LVQPGGSLRL SCAASGYNVI YEDMGWVRQA PGKGLEWVSG
 51       IDVPSGSTYY ADSVKGRFTI SRDNSKNTLY LQMNSLRAED TAVYYCAAVV
101       GQDWFQAEPS EMYYWGQGTL VTVSS

SEQ ID NO: 9-CLEC12A clone 33
  1       QVQLLESGGG LVQPGGSLRL SCAASGDMES YDDMGWVRQA PGKGLEWVSG
 51       IQNTDGSTYY ADSVKGRFTI SRDNSKNTLY LQMNSLRAED TAVYYCATLY
101       DRMVGKEEQL ASWGQGTLVT VSS

SEQ ID NO: 10-CLEC12A clone 40
  1       QVQLLESGGG LVQPGGSLRL SCAASGDTIN PEDMGWVRQA PGKGLEWVSA
 51       IEAQSGSTYY ADSVKGRFTI SRDNSKNTLY LQMNSLRAED TAVYYCARLT
101       AHQEEPVAYW GQGTLVTVSS

SEQ ID NO: 11-CLEC12A clone 56
  1       QVQLLESGGG LVQPGGSLRL SCAASGFTVT DHDMGWVRQA PGKGLEWVSS
 51       ITVGNGSTYY ADSVKGRFTI SRDNSKNTLY LQMNSLRAED TAVYYCATEP
101       LPHQEVTYWG QGTLVTVSS

SEQ ID NO: 12-CLEC12A clone 60
  1       QVQLLESGGG LVQPGGSLRL SCAASGYMFS ADVMSWVRQA PGKGLEWVSG
 51       IWIPDGSTYY ADSVKGRFTI SRDNSKNTLY LQMNSLRAED TAVYYCAAQL
101       NERIASITKN MHSWGQGTLV TVSS
```

-continued

Sequence Listing Free Text

SEQ ID NO: 13-CLEC12A clone 86
1 QVQLLESGGG LVQPGGSLRL SCAASGDMLS AQDMGWVRQA PGKGLEWVSG
51 IDSDDGSTYY ADSVKGRETI SRDNSKNTLY LQMNSLRAED TAVYYCAALW
101 GEDVIMQDSS VGSWGQGTLV TVSS SEQ ID NO: 14-CLEC12A clone consensus sequence
1 QVQLLESGGG LVQPGGSERL SCAASGYXVS XDDMSWVRQA PGKGLEWVSA
51 IXXXDGSTYY ADSVKGRFTI SRDNSKNTLY LQMNSLRAED TAVYYCAXXX
101 XXXXXXXXXX LXYWGQGTLV TVSS
X = any amino acid or no amino acid SEQ ID NO: 15-CLEC12A TriKE amino acid sequence
1 MKWVTFISLL FLESSAYSQV QLVESGGGLV QPGGSLRLSC AASGLTESSY
51 NMGWFRQAPG QGLEAVASIT WSGRDTFYAD SVKGRFTISR DNSKNTLYLQ
101 MNSLRAEDTA VYYCAANPWP VAAPRSGTYW GQGTLVTVSS SGGGGSGGGG
151 SGGGGSGGGG SGNWVNVISD LKKIEDLIQS MHIDATLYTE SDVHPSCKVT
201 AMKCFLLELQ VISLESGDAS IHDTVENLII LANNSLSSNG NVTESGCKEC
251 EELEEKNIKE FLQSFVHIVQ MFINTSGSTS GSGKPGSGEG STKGQVQLQE
301 SGPGLVKPSE TLSLTCVVSG GSISSSNWWS WVRQPPGKGL EWIGEIYHSG
351 SPDYNPSLKS RVTISVDKSR NQFSLKLSSV TAADTAVYYC AKVSTGGFFD
401 YWGQGTLVTV SSGGGGSGGG GSGGGGSEIE LTQSPSSLSA SVGDRVTITC
451 RASQSISSYL NWYQQKPGKA PKLLIYAASS LQSGVPSRFS GSGSGTDFTL
501 TISSLQPEDF ATYYCQQSYS TPPTFGPGTK VEI
underlined: signal peptide
bold: anti-CLEC12A scFv SEQ ID NO: 16-Clone 1 DNA sequence
1 CAGGTGCAGC TGCAGGAGTC TGGGGGAGGC TTGGTACAGC CTGGGGGGTC CCTGCGTCTC
61 TCCTGTGCAG CCTCCGGAGA TAGGTTTAGC AATGACGTTA TGGCCTGGGT CCGCCAGGCT
121 CCAGGGAAGG GTCTAGAGTG GGTATCAGCC ATTGTTACCC AAGACGGTAG CACATACTAC
181 GCAGACTCCG TGAAGGGCCG GTTCACCATC TCCCGTGACA ATTCCAAGAA CACGCTGTAT
241 CTGCAAATGA ACAGCCTGCG TGCCGAGGAC ACCGCGGTAT ATTATTGCGC GGGAGAGCCT
301 CTTGATGCCG AGGACTTGTG GTATTGGGGT CAGGGAACCC TGGTCACCGT CTCGAGC SEQ ID NO: 17-Clone 3 DNA sequence
1 CAGGTGCAGC TGTTGGAGTC TGGGGGAGGC TTGGTACAGC CTGGGGGGTC CCTGCGTCTC
61 TCCTGTGCAG CCTCCGGAGT TAGGGTTAGC GCTCAGTTTA TGAGCTGGGT CCGCCAGGCT
121 CCAGGGAAGG GTCTAGAGTG GGTATCAAGC ATTTATAAGA AAAACGGTAG CACATACTAC
181 GCAGACTCCG TGAAGGGCCG GTTCACCATC TCCCGTGACA ATTCCAAGAA CACGCTGTAT
241 CTGCAAATGA ACAGCCTGCG TGCCGAGGAC ACCGCGGTAT ATTATTGCGC GATTGATCAT
301 GGGGAGGAGC ACAAGGAGCT GTACTCTTGG GGTCAGGGAA CCCTGGTCAC CGTCTCGAGC SEQ ID NO: 18-Clone 9 DNA sequence
1 CAGGTGCAGC TGTTGGAGTC TGGGGGAGGC TTGGTACAGC CTGGGGGGTC CCTGCGTCTC
61 TCCTGTGCAG CCTCCGGATA TAGCATTACC GATCAGGATA TGAGCTGGGT CCGCCAGGCT
121 CCAGGGAAGG GTCTAGAGTG GGTATCAGGC ATTCTGGCCA CAAGCGGTAG CACATACTAC
181 GCAGACTCCG TGAAGGGCCG GTTCACCATC TCCCGTGACA ATTCCAAGAA CACGCTGTAT
241 CTGCAAATGA ACAGCCTGCG TGCCGAGGAC ACCGCGGTAT ATTATTGCGC GGGAGAGGTT
301 GAGAAGAGTT CCCAGTCGAT GCCGTTTTGG GGTCAGGGAA CCCTGGTCAC CGTCTCGAGC SEQ ID NO: 19-Clone 10 DNA sequence
1 CAGGTGCAGC TGTTGGAGTC TGGGGGAGGC TTGGTACAGC CTGGGGGGTC CCTGCGTCTC
61 TCCTGTGCAG CCTCCGGAGT TAACGTTACC GCTGACGATA TGAGCTGGGT CCGCCAGGCT
121 CCAGGGAAGG GTCTAGAGTG GGTATCAACC ATTGATGGCG GTGACGGTAG CACATACTAC
181 GCAGACTCCG TGAAGGGCCG GTTCACCATC TCCCGTGACA ATTCCAAGAA CACGCTGTAT
241 CTGCAAATGA ACAGCCTGCG TGCCGAGGAC ACCGCGGTAT ATTATTGCGC GACTGCTTTT
301 ACGTCGCATG AGGCGGAGGT CCACTCTTGG GGTCAGGGAA CCCTGGTCAC CGTCTCGAGC SEQ ID NO: 20-Clone 11 DNA sequence
1 CAGGTGCAGC TGTTGGAGTC TGGGGGAGGC TTGGTACAGC CTGGGGGGTC CCTGCGTCTC
61 TCCTGTGCAG CCTCCGGATA TAGGCTTAGC AATGACATTA TGGCCTGGGT CCGCCAGGCT
121 CCAGGGAAGG GTCTAGAGTG GGTATCAGCC ATTGTGGACA CAGACGGTAG CACATACTAC
181 GCAGACTCCG TGAAGGGCCG GTTCACCATC TCCCGTGACA ATTCCAAGAA CACGCTGTAT
241 CTGCAAATGA ACAGCCTGCG TGCCGAGGAC ACCGCGGTAT ATTATTGCGC GAGAGATCCT
301 TATAATGAGG ACGACGTCAG CTATTGGGGT CAGGGAACCC TGGTCACCGT CTCGAGC SEQ ID NO: 21-Clone 17 DNA sequence
1 CAGGTGCAGC TGTTGGAGTC TGGGGGAGGC TTGGTACAGC CTGGGGGGTC CCTGCGTCTC
61 TCCTGTGCAG CCTCCGGATT TAGGTTTATC GCTCAGGATA TGAGCTGGGT CCGCCAGGCT
121 ACAGGGAAGG GTCTAGAGTG GGTATCAACC ATTGCTACGA ATGACGGTAG CACATACTAC
181 GCAGACTCCG TGAAGGGCCG GTTCACCATC TCCCGTGACA ATTCCAAGAA CACGCTGTAT
241 CTGCAAATGA ACAGCCTGCG TGCCGAGGAC ACCGCGGTAT ATTATTGCGC GACTGATTCG
301 TCTTGGGAGA ACGACTTGTG GTATTGGGGT CAGGGAACCC TGGTCACCGT CTCGAGC -continued

| Sequence Listing Free Text |
|---|

SEQ ID NO: 22-Clone 23 DNA sequence
```
  1   CAGGTGCAGC TGTTGGAGTC TGGGGGAGGC TTGGTACAGC CTGGGGGGTC CCTGCGTCTC
 61   TCCTGTGCAG CCTCCGGATT TAGGCTTACC GATGAGGATA TGAGCTGGGT CCGCCAGGCT
121   CCAGGGAAGG GTCTAGAGTG GGTATCAACC ATTGCTACCA GAGACGGTAG CACATACTAC
181   GCAGACTCCG TGAAGGGCCG GTTCACCATC TCCCGTGACA ATTCCAAGAA CACGCTGTAT
241   CTGCAAATGA ACAGCCTGCG TGCCGAGGAC ACCGCGGTAT ATTATTGCGC GGGACTTAGG
301   GATCAGTTGT ATGGGAACGA GCAGTTGGCC TTTTGGGGTC AGGGAACCCT GGTCACCGTC
361   TCGAGC
```

SEQ ID NO: 23-Clone 29 DNA sequence
```
  1   CAGGTGCAGC TGTTGGAGTC TGGGGGAGGC TTGGTACAGC CTGGGGGGTC CCTGCGTCTC
 61   TCCTGTGCAG CCTCCGGATA TAACGTTATC TATGAGGATA TGGGCTGGGT CCGCCAGGCT
121   CCAGGGAAGG GTCTAGAGTG GGTATCAGGC ATTGATGTCC CTAGCGGTAG CACATACTAC
181   GCAGACTCCG TGAAGGGCCG GTTCACCATC TCCCGTGACA ATTCCAAGAA CACGCTGTAT
241   CTGCAAATGA ACAGCCTGCG TGCCGAGGAC ACCGCGGTAT ATTATTGCGC GGCTGTTGTT
301   GGTCAGGATT GGTTTCAGGC TGAGCCCTCG GAGATGTACT ATTGGGGTCA GGGAACCCTG
361   GTCACCGTCT CGAGC
```

SEQ ID NO: 24-Clone 33 DNA sequence
```
  1   CAGGTGCAGC TGTTGGAGTC TGGGGGAGGC TTGGTACAGC CTGGGGGGTC CCTGCGTCTC
 61   TCCTGTGCAG CCTCCGGAGA TATGTTTAGC TATGACGATA TGGGCTGGGT CCGCCAGGCT
121   CCAGGGAAGG GTCTAGAGTG GGTATCAGGC ATTCAGAACA CTGACGGTAG CACATACTAC
181   GCAGACTCCG TGAAGGGCCG GTTCACCATC TCCCGTGACA ATTCCAAGAA CACGCTGTAT
241   CTGCAAATGA ACAGCCTGCG TGCCGAGGAC ACCGCGGTAT ATTATTGCGC GACTCTGTAT
301   GATAGGATGG TTGGGAAGGA GGAGCAGTTG GCCTCTTGGG GTCAGGGAAC CCTGGTCACC
361   GTCTCGAGC
```

SEQ ID NO: 25-Clone 40 DNA sequence
```
  1   CAGGTGCAGC TGTTGGAGTC TGGGGGAGGC TTGGTACAGC CTGGGGGGTC CCTGCGTCTC
 61   TCCTGTGCAG CCTCCGGAGA TACCATTAAC CCTGAGGATA TGGGCTGGGT CCGCCAGGCT
121   CCAGGGAAGG GTCTAGAGTG GGTATCAGCC ATTGAGGCGC AAAGCGGTAG CACATACTAC
181   GCAGACTCCG TGAAGGGCCG GTTCACCATC TCCCGTGACA ATTCCAAGAA CACGCTGTAT
241   CTGCAAATGA ACAGCCTGCG TGCCGAGGAC ACCGCGGTAT ATTATTGCGC GAGATTGACT
301   GCTCATCAGG AGGAGCCGGT CGCGTATTGG GGTCAGGGAA CCCTGGTCAC CGTCTCGAGC
```

SEQ ID NO: 26-Clone 56 DNA sequence
```
  1   CAGGTGCAGC TGTTGGAGTC TGGGGGAGGC TTGGTACAGC CTGGGGGGTC CCTGCGTCTC
 61   TCCTGTGCAG CCTCCGGATT TACGGTTACC GATCACGATA TGGGCTGGGT CCGCCAGGCT
121   CCAGGGAAGG GTCTAGAGTG GGTATCAAGC ATTACTGTGG GAAACGGTAG CACATACTAC
181   GCAGACTCCG TGAAGGGCCG GTTCACCATC TCCCGTGACA ATTCCAAGAA CACGCTGTAT
241   CTGCAAATGA ACAGCCTGCG TGCCGAGGAC ACCGCGGTAT ATTATTGCGC GACAGAGCCT
301   TTGCCGCACC AGGAGGTCAC GTATTGGGGT CAGGGAACCC TGGTCACCGT CTCGAGC
```

SEQ ID NO: 27-Clone 60 DNA sequence
```
  1   CAGGTGCAGC TGTTGGAGTC TGGGGGAGGC TTGGTACAGC CTGGGGGGTC CCTGCGTCTC
 61   TCCTGTGCAG CCTCCGGATA TATGTTTAGC GCTGACGTTA TGAGCTGGGT CCGCCAGGCT
121   CCAGGGAAGG GTCTAGAGTG GGTATCAGGC ATTTGGATCC CTGACGGTAG CACATACTAC
181   GCAGACTCCG TGAAGGGCCG GTTCACCATC TCCCGTGACA ATTCCAAGAA CACGCTGTAT
241   CTGCAAATGA ACAGCCTGCG TGCCGAGGAC ACCGCGGTAT ATTATTGCGC GGCTCAGCTG
301   AATGAGAGGA TTGCTTCTAT TACGAAGAAC ATGCACTCTT GGGGTCAGGG AACCCTGGTC
361   ACCGTCTCGA GC
```

SEQ ID NO: 28-Clone 86 DNA sequence
```
  1   CAGGTGCAGC TGTTGGAGTC TGGGGGAGGC TTGGTACAGC CTGGGGGGTC CCTGCGTCTC
      TCCTGTGCAG CCTCCGGAGA TATGCTTAGC GCTCAGGATA TGGGCTGGGT CCGCCAGGCT
 61   CCAGGGAAGG GTCTAGAGTG GGTATCAGGC ATTGATAGCG ATGACGGTAG CACATACTAC
121   GCAGACTCCG TGAAGGGCCG GTTCACCATC TCCCGTGACA ATTCCAAGAA CACGCTGTAT
181   CTGCAAATGA ACAGCCTGCG TGCCGAGGAC ACCGCGGTAT ATTATTGCGC GGCATTGTGG
241   GGGGAGGATG TGATTATGCA GGACTCGTCG GTGGGGTCTT GGGGTCAGGG AACCCTGGTC
301   ACCGTCTCGA GC
```

SEQ ID NO: 29-CDR1

$X_1X_2X_3MX_4$ $X_1$ = N, A, D, Y, or P $X_2$ = D, E, H, Q, or deletion $X_3$ = V, F, I, or D $X_4$ = A, S, or G

SEQ ID NO: 30-CDR2

$X_1IX_2X_3X_4X_5$GSTY YADSVKGRFT $X_1$ = A, S, T, or G $X_2$ = V, Y, L, D, A, E, T, W, Q, or deletion $X_3$ = T, K, A, G, D, V, N, I, or S $X_4$ = Q, K, T, G, N, R, P, or D $X_5$ = D, N, or S -continued Sequence Listing Free Text SEQ ID NO: 31-CDR3
$X_1X_2X_3X_4X_5X_6X_7X_8X_9X_{10}X_{11}X_{12}X_{13}X_{14}X_{15}X_{16}$
$X_1$ = any amino acid or deletion
$X_2$ = any amino acid or deletion
$X_3$ = any amino acid or deletion
$X_4$ = P, E, S, Q, R, or H
$X_5$ = any amino acid or deletion
$X_6$ = any amino acid or deletion
$X_7$ = any amino acid or deletion
$X_8$ = any amino acid or deletion
$X_9$ = any amino acid or deletion
$X_{10}$ = any amino acid or deletion
$X_{11}$ = any amino acid or deletion
$X_{12}$ = any amino acid or deletion
$X_{13}$ = any amino acid or deletion
$X_{14}$ = L, M, or V
$X_{15}$ = W, Y, P, H, S, A, T, or G
$X_{16}$ = Y, S, or F SEQ ID NO: 32-Signal peptide
MKWVTFISLL FLESSAYS SEQ ID NO: 33-Histidine tag, including spacer
VDEHHHHHHH HHH SEQ ID NO: 34-CD16-huCAM Clone 33 bi-specific compound
KWVTFISLLF LESSAYSQVQ LVESGGGLVQ PGGSLRLSCA ASGLTESSYN MGWERQAPGQ
GLEAVASITW SGRDTFYADS VKGRFTISRD NSKNTLYLQM NSLRAEDTAV YYCAANPWPV
AAPRSGTYWG QGTLVTVSSS GGGGSGGGGS GGGGSGGGGS GGSQVQLLES GGGLVQPGGS
LRLSCAASGD MFSYDDMGWV RQAPGKGLEW VSGIQNTDGS TYYADSVKGR FTISRDNSKN
TLYLQMNSLR AEDTAVYYCA TLYDRMVGKE EQLASWGQGT LVTVSSGSHH HHHHHHHH
underline: signal sequence
double underline: HuEF91
Bold: anti-CLEC12A Clone 33

SEQ ID NO: 35-CD16-huCAM Clone 33 tri-specific compound
KWVTFISLLF LESSAYSQVQ LVESGGGLVQ PGGSLRLSCA ASGLTESSYN MGWERQAPGO
GLEAVASITW SGRDTFYADS VKGRFTISRD NSKNTLYLQM NSLRAEDTAV YYCAANPWPV
AAPRSGTYWG QGTLVTVSSS GGGGSGGGGS GGGGSGGGGS GNWVNVISDL KKIEDLIQSM
HIDATLYTES DVHPSCKVTA MKCFLLELQV ISLESGDASI HDTVENLIIL ANNSLSSNGN
VTESGCKECE ELEEKNIKEF LQSFVHIVQM FINTSGSTSG SGKPGSGEGS TKGGSQVQLL
ESGGGLVQPG GSLRLSCAAS GDMFSYDDMG WVRQAPGKGL EWVSGIQNTD GSTYYADSVK
GRFTISRDNS KNTLYLQMNS LRAEDTAVYY CATLYDRMVG KEEQLASWGQ GTLVTVSSGS
HHHHHHHHHH
underline: signal sequence
double underline: HuEF91
hashed underline: human IL-15 fragment
bold: anti-CLEC12A Clone 33

SEQ ID NO: 36-Whitlow linker
GSTSGSGKPG SGEGSTKG

What is claimed is:

1. A CLEC12A single-domain antibody comprising:

complementarity-determining region (CDR) 1 as set forth in amino acids 31-35 of SEQ ID NO: 1, CDR2 as set forth in amino acids 50-69 of SEQ ID NO:1, and CDR3 as set forth in amino acids 98-108 of SEQ ID NO:1;

CDR 1 as set forth in amino acids 31-35 of SEQ ID NO:2, CDR2 as set forth in amino acids 50-69 of SEQ ID NO:2, and CDR3 as set forth in amino acids 99-109 of SEQ ID NO:2;

CDR1 as set forth in amino acids 31-35 of SEQ ID NO:3, CDR2 as set forth in amino acids 50-69 of SEQ ID NO:3, and CDR3 as set forth in amino acids 99-109 of SEQ ID NO:3;

CDR1 as set forth in amino acids 31-35 of SEQ ID NO:4, CDR2 as set forth in amino acids 50-69 of SEQ ID NO:4, and CDR3 as set forth in amino acids 99-109 of SEQ ID NO:4;

CDR1 as set forth in amino acids 31-35 of SEQ ID NO:5, CDR2 as set forth in amino acids 50-69 of SEQ ID NO:5, and CDR3 as set forth in amino acids 98-108 of SEQ ID NO:5;

CDR1 as set forth in amino acids 31-35 of SEQ ID NO:6, CDR2 as set forth in amino acids 50-69 of SEQ ID NO:6, and CDR3 as set forth in amino acids 98-108 of SEQ ID NO:6;

CDR1 as set forth in amino acids 31-35 of SEQ ID NO:7, CDR2 as set forth in amino acids 50-69 of SEQ ID NO:7, and CDR3 as set forth in amino acids 99-111 of SEQ ID NO:7;

CDR1 as set forth in amino acids 31-35 of SEQ ID NO:8, CDR2 as set forth in amino acids 50-69 of SEQ ID NO:8, and CDR3 as set forth in amino acids 99-114 of SEQ ID NO:8;

CDR1 as set forth in amino acids 31-35 of SEQ ID NO:9, CDR2 as set forth in amino acids 50-69 of SEQ ID NO:9, and CDR3 as set forth in amino acids 99-112 of SEQ ID NO:9;

CDR1 as set forth in amino acids 31-35 of SEQ ID NO:10, CDR2 as set forth in amino acids 50-69 of SEQ ID NO:10, and CDR3 as set forth in amino acids 99-109 of SEQ ID NO:10;

CDR1 as set forth in amino acids 31-35 of SEQ ID NO:11, CDR2 as set forth in amino acids 50-69 of SEQ ID NO:11, and CDR3 as set forth in amino acids 99-108 of SEQ ID NO:11;

CDR1 as set forth in amino acids 31-35 of SEQ ID NO:12, CDR2 as set forth in amino acids 50-69 of SEQ ID NO:12, and CDR3 as set forth in amino acids 99-112 of SEQ ID NO:12; or CDR1 as set forth in amino acids 31-35 of SEQ ID NO:13, CDR2 as set forth in amino acids 50-69 of SEQ ID NO: 13, and CDR3 as set forth in amino acids 99-113 of SEQ ID NO:13.

2. The CLEC12A single-domain antibody of claim 1, wherein the antibody comprises:

the amino acid sequence of SEQ ID NO:1;
the amino acid sequence of SEQ ID NO:2;
the amino acid sequence of SEQ ID NO:3;
the amino acid sequence of SEQ ID NO:4;
the amino acid sequence of SEQ ID NO:5;
the amino acid sequence of SEQ ID NO:6;
the amino acid sequence of SEQ ID NO:7;
the amino acid sequence of SEQ ID NO:8;
the amino acid sequence of SEQ ID NO:9;
the amino acid sequence of SEQ ID NO: 10;
the amino acid sequence of SEQ ID NO:11;
the amino acid sequence of SEQ ID NO: 12; or
the amino acid sequence of SEQ ID NO:13.

3. The CLEC12A single-domain antibody of claim 1, wherein:

the CLEC12A single-domain antibody comprises an amino acid sequence having at least 90% identity to the amino acid sequence of SEQ ID NO:1;

the CLEC12A single-domain antibody comprises an amino acid sequence having at least 90% identity to the amino acid sequence of SEQ ID NO:2;

the CLEC12A single-domain antibody comprises an amino acid sequence having at least 90% identity to the amino acid sequence of SEQ ID NO:3;

the CLEC12A single-domain antibody comprises an amino acid sequence having at least 90% identity to the amino acid sequence of SEQ ID NO:4;

the CLEC12A single-domain antibody comprises an amino acid sequence having at least 90% identity to the amino acid sequence of SEQ ID NO:5;

the CLEC12A single-domain antibody comprises an amino acid sequence having at least 90% identity to the amino acid sequence of SEQ ID NO:6;

the CLEC12A single-domain antibody comprises an amino acid sequence having at least 90% identity to the amino acid sequence of SEQ ID NO:7;

the CLEC12A single-domain antibody comprises an amino acid sequence having at least 90% identity to the amino acid sequence of SEQ ID NO:8;

the CLEC12A single-domain antibody comprises an amino acid sequence having at least 90% identity to the amino acid sequence of SEQ ID NO:9;

the CLEC12A single-domain antibody comprises an amino acid sequence having at least 90% identity to the amino acid sequence of SEQ ID NO:10;

the CLEC12A single-domain antibody comprises an amino acid sequence having at least 90% identity to the amino acid sequence of SEQ ID NO:11;

the CLEC12A single-domain antibody comprises an amino acid sequence having at least 90% identity to the amino acid sequence of SEQ ID NO: 12; or the CLEC12A single-domain antibody comprises an amino acid sequence having at least 90% identity to the amino acid sequence of SEQ ID NO:13.

4. A biologic therapeutic compound comprising the CLEC12A single-domain antibody of claim 1.

5. The biologic therapeutic compound of claim 4, wherein the biologic therapeutic compound is:

a bi-specific Killer engager molecule (BiKE);
a tri-specific Killer engager molecule (TriKE);
a tetra-specific Killer engager molecule (TetraKE);
a penta-specific Killer engager molecule (PentaKE);
a bi-specific T cell engager molecule (BiTE);
a tri-specific T cell engager molecule (TriTE);
tetra-specific T cell engager molecule (TetraTE);
a penta-specific T cell engager molecule (PentaTE);
a chimeric antigen receptor;
a full antibody;
an antibody-drug conjugate (ADC) molecule;
a targeted delivery construct; or
a labeling construct.

6. A pharmaceutical composition comprising: the biologic therapeutic compound of claim 4; and a pharmaceutically acceptable carrier.

7. A method comprising:

administering to a subject having a tumor characterized in expression of CLEC12A a biologic therapeutic compound of claim 4 in an amount to ameliorate at least one symptom or clinical sign of the tumor.

8. The method of claim 7, wherein the biological therapeutic compound is:

a bi-specific Killer engager molecule (BiKE);
a tri-specific Killer engager molecule (TriKE);
a tetra-specific Killer engager molecule (TetraKE);
a penta-specific Killer engager molecule (PentaKE);
a bi-specific T cell engager molecule (BiTE);
a tri-specific T cell engager molecule (TriTE);
tetra-specific T cell engager molecule (TetraTE);
a penta-specific T cell engager molecule (PentaTE);
a chimeric antigen receptor;
a full antibody;
an antibody-drug conjugate (ADC) molecule; or
a targeted delivery construct.

9. The CLEC12A single-domain antibody of claim 1, wherein the antibody comprises the amino acid sequence of SEQ ID NO:9.

10. The biologic therapeutic compound of claim 4, wherein the biologic therapeutic compound comprises the amino acid sequence of SEQ ID NO: 15, SEQ ID NO: 33, or SEQ ID NO:34.

11. The method of claim 7, wherein the biologic therapeutic compound comprises the amino acid sequence of SEQ ID NO:15, SEQ ID NO:33, or SEQ ID NO: 34.

12. A pharmaceutical composition comprising the biologic therapeutic compound of claim 4 and a pharmaceutically acceptable carrier.

13. A method comprising:

administering to a subject having a tumor characterized in expression of CLEC12A a biologic therapeutic compound of claim 4 in an amount to ameliorate at least one symptom or clinical sign of the tumor.

* * * * *